(12) United States Patent
Inada et al.

(10) Patent No.: US 7,211,193 B2
(45) Date of Patent: May 1, 2007

(54) PROCESSES FOR THE PURIFICATION OF BIS(2-HYDROXYETHYL)TEREPHTHALATE

(75) Inventors: Shuji Inada, Tokyo (JP); Kikuchi Sato, Fukuyama (JP)

(73) Assignee: Pet Rebirth Co., Ltd. (JP)

( * ) Notice: Subject to any disclaimer, the term of this patent is extended or adjusted under 35 U.S.C. 154(b) by 399 days.

(21) Appl. No.: 10/481,989

(22) PCT Filed: May 30, 2003

(86) PCT No.: PCT/JP03/06878

§ 371 (c)(1),
(2), (4) Date: Dec. 24, 2003

(87) PCT Pub. No.: WO03/101929

PCT Pub. Date: Dec. 11, 2003

(65) Prior Publication Data

US 2004/0182782 A1    Sep. 23, 2004

(30) Foreign Application Priority Data

Jun. 4, 2002 (JP) .............................. 2002-163221
Feb. 3, 2003 (JP) .............................. 2003-026123

(51) Int. Cl.
  *B01D 11/00* (2006.01)
  *C08J 11/04* (2006.01)
(52) U.S. Cl. .......................... 210/634; 23/299; 203/39; 203/89; 210/774; 210/806; 521/48; 528/308.1
(58) Field of Classification Search ...... 23/295 R–300; 210/634, 639, 768–771, 774, 806, 767; 203/37–47, 203/71, 73, 74, 89, 91, 72, 80, 88; 264/37.1, 264/37.18, 37.19, 918; 521/48; 528/308.1–309.1; 560/76–78, 96; 159/47.1, 49, DIG. 8
See application file for complete search history.

(56) References Cited

U.S. PATENT DOCUMENTS 3,577,454 A    5/1971    Keck et al.

(Continued)

FOREIGN PATENT DOCUMENTS

EP    1120394 A1    8/2001

(Continued)

OTHER PUBLICATIONS

WO 01/10812 International Search Report.

(Continued)

*Primary Examiner*—Joseph Drodge
(74) *Attorney, Agent, or Firm*—Anderson Kill & Olick, PC

(57) ABSTRACT

A method is disclosed for efficiently obtaining BHET of high purity from an EG (ethylene glycol) solution containing crude BHET (bis(2-hydroxyethyl)terephthalate), especially a decomposition product solution obtained by decomposing a polyester containing PET (polyethylene terephthalate) as a main component, by use of EG, while minimizing by-production of impurity components such as DEG (diethylene glycol), DEG ester and oligomers. The decomposition product solution is subjected to crystallization and solid-liquid separation under specific temperature conditions. Further, in accordance with the invention, a method of purifying BHET is taught which comprises evaporation steps of evaporating low-boiling-point components from the decomposition product solution under specific conditions so as to obtain a melt solution and a molecular distillation step of distilling the obtained melt solution under specific conditions so as to obtain a specific fraction.

29 Claims, 1 Drawing Sheet

U.S. PATENT DOCUMENTS

| | | | |
|---|---|---|---|
| 3,668,235 A | * | 6/1972 | Ichikawa et al. ............. 560/79 |
| 3,803,003 A | | 4/1974 | Matsuzawa et al. |
| 4,683,034 A | * | 7/1987 | Bader et al. ................. 560/78 |
| 5,498,749 A | * | 3/1996 | Heise et al. .................. 560/78 |
| 5,554,657 A | * | 9/1996 | Brownscombe et al. ...... 521/48 |
| 5,635,584 A | * | 6/1997 | Ekart et al. ................. 528/271 |
| 6,410,607 B1 | * | 6/2002 | Ekart et al. ................ 521/48.5 |
| 6,630,601 B1 | * | 10/2003 | Inada et al. ................... 560/76 |
| 6,710,202 B2 | * | 3/2004 | Inada et al. ................... 560/78 |

FOREIGN PATENT DOCUMENTS

| | | |
|---|---|---|
| EP | 1306364 A1 | 5/2003 |
| GB | 1143072 | 2/1969 |
| JP | 2000-53802 | 2/2000 |
| JP | 2000-169623 | 6/2000 |
| JP | 2000-239233 | 9/2000 |
| JP | 2001-018224 | 1/2001 |
| JP | 2001-048834 | 2/2001 |
| JP | 2001-048835 | 2/2001 |
| JP | 2001-048836 | 2/2001 |
| JP | 2001-048837 | 2/2001 |
| JP | 2001-322967 | 11/2001 |
| JP | 2001-335539 | 12/2001 |
| JP | 2002-121173 | 4/2002 |

OTHER PUBLICATIONS

WO 01/19775 International Search Report.
WO 01/29110 International Search Report.
WO 01/56970 International Search Report.
WO 02/10117 International Search Report.
Japanese Patent Laid-Open Publication No. 48-96546, dated Dec. 10, 1973.

* cited by examiner

PROCESSES FOR THE PURIFICATION OF BIS(2-HYDROXYETHYL)TEREPHTHALATE

TECHNICAL FIELD

The present invention relates to a method for purifying bis(2-hydroxyethyl)terephthalate. More specifically, it relates to a purification method for obtaining bis(2-hydroxyethyl)terephthalate of high quality efficiently by subjecting an ethylene glycol solution of crude bis(2-hydroxyethyl) terephthalate containing 2-hydroxyethyl[2-(2-hydroxyethoxy)ethyl]terephthalate and an oligomer as impurities to crystallization and/or distillation under specific conditions.

BACKGROUND ART

Polyesters, a polyethylene terephthalate (hereinafter may be abbreviated as "PET") in particular, are used in fields of various molded articles such as fibers, films and resins. PET is generally produced by a method of reacting dimethyl terephthalate or terephthalic acid with ethylene glycol (hereinafter may be abbreviated as "EG") in the presence of catalysts. In the production of PET, to satisfy properties required for a particular application, functional additives such as a stabilizer, a coloring agent, an antistatic agent and an ultraviolet absorber are added. Recently in particular, when PET is used in a container for a beverage, properties such as an ultraviolet blocking property and a gas barrier property are required depending on the type of the content so as to maintain quality thereof. As measures for attaining such properties, measures such as mixing an ultraviolet absorber or a gas barrier polymer into PET and laminating thin layers of the polymer so as to form a multilayered container are taken.

Meanwhile, disposal of used polyethylene terephthalate molded articles, polyethylene terephthalate bottles (PET bottles) in particular, has become a social problem from the viewpoint of environmental destruction, and recovery and recycle of the bottles are promoted.

As a method for recycling the bottles, a so-called material recycle method has been practically used which comprises the steps of recovering post-consumer PET bottles, crushing the bottles into chips or flakes and washing and cleaning the chips or flakes so as to use them as molding raw materials for other molded articles. As for PET as molding raw materials obtained by this method, it is very difficult to prevent foreign materials such as metals, glass and resins different from PET from mixing into PET or remove the foreign materials at a low cost. The foreign materials are a problem since they cause a reduction in production efficiency in production of other molded articles, deterioration in quality of product, and an increase in production costs. Further, in the case of this method, when colored PET bottles are included in the collected PET bottles, it is expensive to separate the colored bottles from uncolored bottles, thereby causing an increase in costs of the molding raw materials. To avoid this, the colored PET bottles are no longer used, and colored labels are labeled on the bodies of transparent PET bottles instead. However, this means also has a problem that the colored labels impair the appearances of the bottles and increase the costs, whereby the effect of the colored labels is not satisfactory. Further, in the case of transparent PET bottles having other polymers contained therein or laminated thereon so as to be given functionality, it is very difficult to separate the bottles from other bottles.

Other methods for recycling PET bottles have also been studied, and one of the studied methods is a chemical recycle method. With respect to recycling of the PET bottles by this method, the present inventors have studied a method for producing high-purity bis(2-hydroxyethyl)terephthalate (hereinafter may be abbreviated as "BHET") by depolymerizing chips or flakes obtained by crushing collected PET bottles by use of an excess of ethylene glycol and purifying the obtained decomposition product solution (depolymerization reaction product solution: EG solution). As a result, they have found and already proposed that high-purity BHET can be obtained by purifying the above reaction product solution by a combination of decolorization, deionization, crystallization, distillation, and other treatments (refer to Patent Documents 1 to 16).

| (Patent Document 1) | JP-A-2000-53802 |
| --- | --- |
| (Patent Document 2) | JP-A-2000-169623 |
| (Patent Document 3) | JP-A-2000-239233 |
| (Patent Document 4) | JP-A-2001-18224 |
| (Patent Document 5) | JP-A-2001-48834 |
| (Patent Document 6) | JP-A-2001-48835 |
| (Patent Document 7) | JP-A-2001-48836 |
| (Patent Document 8) | JP-A-2001-48837 |
| (Patent Document 9) | JP-A-2001-322967 |
| (Patent Document 10) | JP-A-2001-335539 |
| (Patent Document 11) | JP-A-2002-121173 |
| (Patent Document 12) | International Publication No. 01/10812 pamphlet |
| (Patent Document 13) | International Publication No. 01/19775 pamphlet |
| (Patent Document 14) | International Publication No. 01/29110 pamphlet |
| (Patent Document 15) | International Publication No. 01/56970 pamphlet |
| (Patent Document 16) | International Publication No. 02/10117 pamphlet |

(The term "JP-A" as used herein means an "unexamined published Japanese patent application")

The present inventors have further studied a further improvement in purification efficiency and a further improvement in quality in this method. As a result, they have found that impurity components other than BHET, particularly a diethylene glycol (hereinafter may be abbreviated as "DEG") and components used so as to impart functionality cause deterioration in quality of BHET. Thus, the present inventors have studied keeping the contents of these components in a product BHET as low as possible.

Since the DEG component and functionality-imparting components are contained in starting materials (PET bottles) of chemical recycle, these components must be removed efficiently with a side reaction kept from occurring.

Further, the DEG component is not only by-produced in the depolymerization step but also produced by dehydration condensation of EG during purification of the decomposition product solution, e.g., during deionization of the solution. Further, 2-hydroxyethyl[2-(2-hydroxyethoxy)ethyl]terephthalate (hereinafter may be referred to as "DEG ester") produced by an ester interchange reaction between DEG and BHET also causes deterioration in the quality of BHET. However, since the characteristic of the DEG component is very close to that of EG or BHET, it is very difficult to isolate and remove the DEG component from a product BHET.

As a result of studying a method for purifying BHET efficiently, the present inventors have found that the contents of the DEG component and functionality-imparting components in a precipitate can be rendered low depending on crystallization conditions of the decomposition product solution.

Further, when BHET containing large amounts of the DEG component and the functionality-imparting components is subjected to molecular distillation, it must be allowed that the DEG component and the functionality-imparting components exist in a product BHET in large amounts or that the yield of the product is rendered low. The present inventors have found it effective for preventing this that removal of the DEG component and functionality-imparting components or prevention of by-production of the DEG component and functionality-imparting components is achieved as much as possible before the molecular distillation step.

Further, the present inventors have also found that crystallization of BHET is affected by the electric conductivity of the decomposition product solution when BHET is crystallized from the decomposition product solution and that for increasing the sizes of crystals of the precipitate so as to facilitate solid-liquid separation, it is effective to render the electric conductivity small.

The present inventors have also found that when BHET is distilled so as to be purified, a polycondensation reaction proceeds due to exposure of BHET to high temperatures, and an oligomer having a polymerization degree of 2 to 20 is by-produced.

Thus, an object of the present invention is to provide a purification method of obtaining high-purity BHET from an EG solution containing crude BHET, particularly a decomposition product solution which is obtained by decomposition of a polyester containing PET as a main component with EG and contains BHET as a main solute and EG as a main solvent, while minimizing by-production of impurity components, particularly DEG, DEG ester and oligomers, during a purification process and by separating these impurity components efficiently.

Another object of the present invention is to provide a method of crystallizing and separating diethylene glycol component and BHET from a decomposition product solution obtained by decomposition of a polyester containing PET as a main component with EG, particularly a solution which is obtained by decomposition of a polyester containing recovered PET as a main component with EG and contains BHET as a main solute and EG as a main solvent.

Another object of the present invention is to provide a method of crystallizing and separations BHET having a low content of gas barrier agent component when BHET contains the component (gas barrier agent component) derived from a gas barrier polymer.

Still another object of the present invention is to provide a method of crystallizing and separating a diethylene glycol component and BHET by subjecting a decomposition product solution obtained by decomposition of a polyester containing PET as a main component with EG, i.e., a solution containing BHET as a main solute and EG as a main solvent to deionization and crystallization treatments. Still another object of the present invention is to provide a method of crystallizing and separating BHET having a lower content of a gas barrier agent component efficiently when BHET contains the gas barrier agent component.

Still another object of the present invention is to provide a method of separating BHET having a lower content of a diethylene glycol component efficiently by subjecting an EG solution containing crude BHET, particularly a decomposition product solution obtained by decomposition of a polyester containing PET as a main component with EG, i.e., a solution containing BHET as a main solute and EG as a main solvent, to solvent removal and molecular distillation.

Still another object of the present invention is to provide a purification method of obtaining high-quality BHET efficiently by subjecting an EG solution containing crude BHET, particularly a decomposition product solution obtained by decomposition of a polyester containing PET as a main component with EG, i.e., a solution containing BHET as a main solute and EG as a main solvent, to specific crystallization and solvent removal treatments and molecular distillation.

Other objects and advantages of the present invention will become apparent from the following description.

DISCLOSURE OF THE INVENTION

According to the present invention, firstly, the above objects of the present invention are achieved by a method (hereinafter referred to as "first method") of purifying bis (2-hydroxyethyl)terephthalate which comprises:

(1) a crystallization step of cooling an ethylene glycol solution containing crude bis(2-hydroxyethyl)terephthalate from a temperature of at least saturation solubility to temperatures ranging from 15 to 30° C. and keeping the solution within the temperature range for at least 1 hour, and (2) a solid-liquid separation step of subjecting a precipitate containing bis(2-hydroxyethyl)terephthalate as a main component to solid-liquid separation while keeping the precipitate within a temperature range of 15 to 30° C. so as to obtain a cake comprising bis(2-hydroxyethyl.) terephthalate as a main component.

Further, according to the present invention, secondly, the above objects of the present invention are achieved by a method (hereinafter referred to as "second method") of purifying bis(2-hydroxyethyl)terephthalate which comprises:

(1) an evaporation step comprising:
(a) a first evaporation step of introducing an ethylene glycol solution containing crude bis(2-hydroxyethyl)terephthalate into a first evaporator and evaporating low-boiling-point components at a temperature of 130 to 170° C. and a pressure of 300 to 1,000 Pa so as to obtain a first melt solution having a total content of ethylene glycol and free diethylene glycol of 3 to 10 wt %, and
(b) a second evaporation step of introducing the first melt solution into a second evaporator and evaporating low-boiling-point components at a temperature of 130 to 170° C. and a pressure of 50 to 250 Pa so as to obtain a second melt solution having a total content of ethylene glycol and free diethylene glycol of not higher than 0.45 wt %, and
(2) a molecular distillation step of introducing the second melt solution into a falling-thin-film type molecular still and distilling the solution at a temperature of 180 to 220° C. and a pressure of not higher than 25 Pa so as to obtain a fraction containing bis(2-hydroxyethyl)terephthalate as a main component and having a 2-hydroxyethyl[2-(2-hydroxyethoxy)ethyl]terephthalate content of not higher than 1.5 wt % and an oligomer content of not higher than 1 wt %.

Further, according to the present invention, thirdly, the above objects of the present invention are achieved by a method (hereinafter referred to as "third method") of purifying bis(2-hydroxyethyl)terephthalate which comprises:

(1) a crystallization step of cooling an ethylene glycol solution containing crude bis(2-hydroxyethyl)terephthalate from a temperature of at least saturation solubility to temperatures ranging from 15 to 30° C. and keeping the solution within the temperature range for at least 1 hour, (2) a solid-liquid separation step of subjecting a precipitate containing bis(2-hydroxyethyl)terephthalate as a main component to solid-liquid separation while keeping the precipitate within a temperature range of 15 to 30° C. so as to obtain a cake comprising bis(2-hydroxyethyl)terephthalate as a main component, (3) an evaporation step comprising:

(a) a first evaporation step of introducing a melt solution of the cake into a first evaporator and evaporating low-boiling-point components at a temperature of 130 to 170° C. and a pressure of 300 to 1,000 Pa so as to obtain a first melt solution having a total content of ethylene glycol and free diethylene glycol of 3 to 10 wt %, and (b) a second evaporation step of introducing the first melt solution into a second evaporator and evaporating low-boiling-point components at a temperature of 130 to 170° C. and a pressure of 50 to 250 Pa so as to obtain a second melt solution having a total content of ethylene glycol and free diethylene glycol of not higher than 0.45 wt %, and (4) a molecular distillation step of introducing the second melt solution into a falling-thin-film type molecular still and distilling the solution at a temperature of 180 to 220° C. and a pressure of not higher than 25 Pa so as to obtain a fraction containing bis(2-hydroxyethyl)terephthalate as a main component and having a 2-hydroxyethyl[2-(2-hydroxyethoxy)ethyl]terephthalate content of not higher than 1.5 wt % and an oligomer content of not higher than 1 wt %.

Hereinafter, the present invention will be further described with reference to specific examples.

BEST MODE FOR CARRYING OUT THE INVENTION

Figure 1:
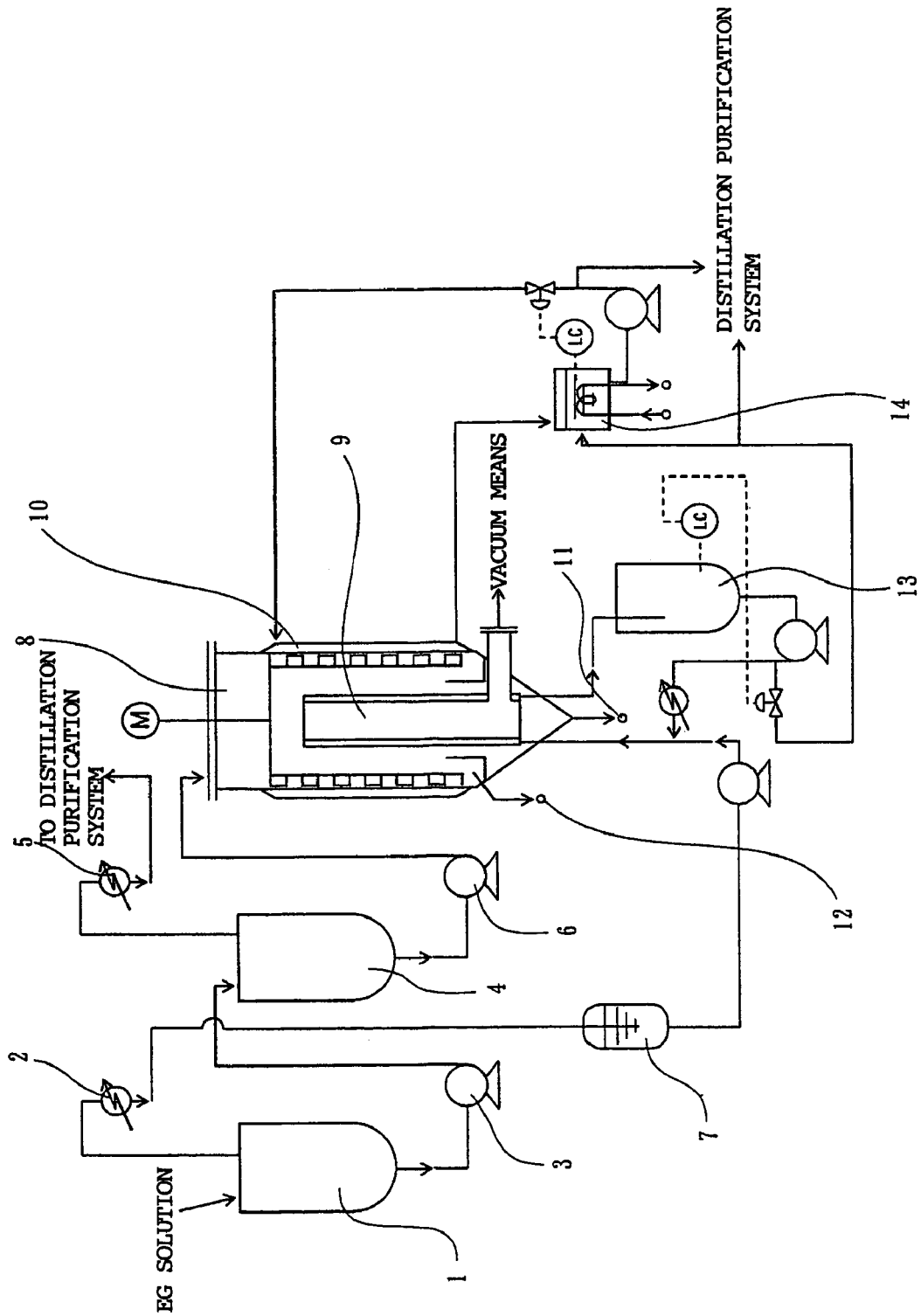
FIG. 1 is a step diagram illustrating a preferred distillation step (combination of components of distiller) in the present invention, wherein reference numeral 1 denotes a first evaporator, 2 a condenser, 3 a melt solution transport pump, 4 a second evaporator, 5 a condenser, 6 a melt solution transport pump, 7 a condensate reservoir, 8 a molecular still, 9 an internal condenser, 10 heating means, 11 a product output port, 12 a distillation pot residue output port, 13 a cooling medium circulating tank, and 14 a heating medium tank.

Firstly, the first method of the present invention will be described.

(Starting Material)

In the first method of the present invention, it is preferred to use, as an EG solution containing crude BHET which is a starting material, an ethylene glycol solution (EG solution) obtained by depolymerizing a terephthalic polyester (PET, in particular) with an excess of EG and subjecting the polyester to an impurity-removing treatment during or after the depolymerization or an EG solution obtained by an esterification reaction between terephthalic acid and EG (preferably a deionized EG solution).

That is, as the EG solution containing crude BHET, a solution obtained by decomposing a polyester containing a polyethylene terephthalate as a main component with ethylene glycol and decolorizing and deionizing the decomposed product is preferably used.

These EG solutions comprise BHET as a main solute and EG as a main solvent. In general, they can contain, as impurity components, at least one component selected from DEG ester (solute component), an oligomer (solute component), DEG (solvent component) and the like. Further, the EG solutions can also contain functionality-imparting components, especially, a gas barrier agent component (solute component).

Of these solutions, the former solution obtained by depolymerizing a terephthalic polyester (PET, in particular) with an excess of EG and subjecting the polyester to an impurity-removing treatment during or after the depolymerization is particularly preferably used. In steps prior to a crystallization step to be described later, these EG solutions are generally handled at temperatures at which solutes are not precipitated (e.g., temperatures higher than 50° C.) and which are not higher than 100° C., preferably at a temperature of 70 to 90° C.

Illustrative examples of the above impurity-removing treatment include a treatment for removing a solid foreign material (such as filtration under heating), a decolorization treatment with activated carbon, and a deionization treatment (cation- or anion-removing treatment) with an ion exchange resin. These foreign material removing treatment, activated carbon treatment and deionization treatment are preferably carried out in the order named. Hence, when the EG solution contains ionized coloring substances, the coloring substances can be removed by the deionization treatment. Further, when the EG solution contains insoluble polymers, the polymers can be removed by filtration under heating.

The above terephthalic polyester is preferably a polyester constituting a PET bottle. As the terephthalic polyester, a post-consumer colored PET bottle which contains an ultraviolet shielding agent at least in a portion thereof can be used.

To say nothing of a homopolymer of PET, the above terephthalic polyester is exemplified by copolymers of PET, e.g., a copolyester obtained by copolymerizing a small amount (for example, not larger than 30 mol %, preferably not larger than 20 mol % based on all acid components) of at least one of other acid components such as aromatic dicarboxylic acids, e.g., isophthalic acid, naphthalenedicarboxylic acid and diphenyldicarboxylic acid, aliphatic dicarboxylic acids, e.g., sebacic acid and adipic acid, and alicyclic dicarboxylic acids e.g., cyclohexanedicarboxylic acid, and other diol components such as 1,4-cyclohexanedimethanol (hereinafter may be abbreviated as "1,4-CHDM"), trimethylene glycol, tetramethylene glycol and hexamethylene glycol. Of these, PET (homopolymer) and copolymers thereof are particularly preferred. These polyesters may be produced by any method.

The above terephthalic polyester may contain other polymers such as a polyethylene isophthalate, a polyethylene naphthalate, a polybutylene terephthalate, a polymethaxylylene adipamide (Nylon MXD 6) and a polyglycolic acid in a small amount (for example, not larger than 40 wt %, preferably not larger than 30 wt %, more preferably not larger than 20 wt % based on all constitutional polymers). Further, the above terephthalic polyester may also contain a catalyst used in a polycondensation reaction of the polyester (such as an antimony compound or a germanium compound), a stabilizer (such as a phosphorus compound), and a colorant (such as phthalocyanine dye, anthraquinone dye, monoazo dye, iron oxide or carbon black).

The above terephthalic polyester may also contain a polymer of a gas barrier layer constituting a multilayered bottle, such as a polymethaxylylene adipamide (Nylon MXD 6) or a polyglycolic acid.

In general, the above terephthalic polyester is decomposed (depolymerized) by use of an excess of EG. The decomposition reaction can be carried out by conventionally known methods and conditions such as methods and conditions which have been previously proposed by the present inventor, including the method and conditions described in the above International Publication No. 01/10812 pamphlet.

To carry out the depolymerization reaction efficiently, it is preferred that the terephthalic polyester be firstly brought into contact with a depolymerization agent (preferably a distillation residue of crude BHET) containing BHET and/or a condensate thereof (preferably an oligomer with an average polymerization degree of 1.1 to 10) as a main component at a high temperature so as to be preliminarily depolymerized (pre-depolymerized) and the depolymerization (actual depolymerization) be furthered by use of an excess of EG and a depolymerization catalyst (e.g., an alkali metal compound) so as to prepare an EG solution containing crude BHET. As the EG, EG containing a small amount of other glycols or EG containing crude EG produced in crystallization and solid-liquid separation of the above EG solution can be used in addition to purified EG. Further, the depolymerization catalyst is preferably used in an amount of 0.1 to 0.5 parts by weight, more preferably 0.15 to 0.4 parts by weight, based on 100 parts by weight of the terephthalic polyester. Illustrative examples of the depolymerization catalyst include sodium hydroxide and sodium methylate.

In the preliminary depolymerization, the ratio of the amount of the terephthalic polyester to the amount of BHET and/or condensate thereof is such that BHET and/or condensate thereof are/is preferably used in an amount of 0.1 to 4.5 parts by weight, more preferably 0.1 to 2.0 parts by weight, particularly preferably 0.1 to 1.0 parts by weight, per part by weight of the terephthalic polyester. The temperature of the preliminary depolymerization is preferably 180 to 290° C., more preferably 190 to 270° C., particularly preferably 200 to 260° C. The reaction time is preferably 0.1 to 5.0 hours, more preferably 0.3 to 1.5 hours. A decomposition product (preliminary depolymerization product) obtained by the preliminary depolymerization preferably has an average polymerization degree of about 2 to 40, more preferably about 5 to 30.

The depolymerization reaction (actual depolymerization reaction) between the preliminary depolymerization product obtained by the preliminary depolymerization and EG is preferably 170 to 265° C., more preferably 190 to 220° C. The ratio between the amount of the preliminary depolymerization product and the amount of EG is such that EG is preferably used in an amount of 0.5 to 8.0 parts by weight, more preferably 2.0 to 7.0 parts by weight, per part by weight of the preliminary depolymerization product. When the amount of the preliminary depolymerization product is too small as compared with the amount of EG, the amount of BHET produced becomes smaller than saturation solubility to EG, so that BHET can be obtained only in an amount smaller than a maximum yield obtained based on a total liquid amount to be deionized, which is uneconomical. On the other hand, when the amount of the preliminary depolymerization product is too large as compared with the amount of EG, an oligomer in BHET increases, thereby lowering the yield of BHET. Further, when BHET exists beyond the saturation solubility of EG, BHET is precipitated, so that deionization cannot be carried out. The depolymerization reaction time is preferably 0.5 to 5.0 hours, more preferably 0.5 to 2.0 hours. The decomposition product solution obtained by the depolymerization is constituted by a solute comprising BHET as a main component and a solvent comprising EG as a main component and may contain an oligomer having a polymerization degree of 2 to 20, particularly 2 to 10, in a small amount (for example, not larger than 20 wt %, particularly not larger than 10 wt %, based on all solutes).

Further, when EG is used as the above depolymerization agent from the beginning, the depolymerization temperature is preferably 170 to 230° C., more preferably 190 to 220° C. The ratio of the amount of the terephthalic polyester to that of EG at the time of depolymerization is preferably 1:9 to 3:7. When the amount of the terephthalic polyester is too small as compared with that of EG, the amount of BHET produced becomes smaller than saturation solubility to EG, so that BHET can be obtained only in an amount smaller than a maximum yield obtained based on a total liquid amount to be deionized, which is uneconomical. On the other hand, when the amount of the terephthalic polyester is too large as compared with that of EG, an oligomer in BHET increases, thereby lowering the yield of BHET. Further, when BHET exists beyond the saturation solubility of EG, BHET is precipitated, so that deionization cannot be carried out.

The above depolymerization is preferably carried out by placing a rectification column on a depolymerization reactor and removing water from the reaction solution to the outside of the system by distillation. At that time, it is preferable to cause evaporated ethylene glycol to return to the system. By carrying out the depolymerization in such a manner, the content of water in the EG solution to be brought into contact with a cation exchanger can be reduced, so that a hydrolysis reaction occurring with the cation-removing treatment can be suppressed. The content of water in the EG solution to be brought into contact with the cation exchanger is preferably adjusted to be 0.5 wt % or lower. The water content is obtained by measuring the EG solution by means of an MK-SS type Karl Fischer moisture meter manufactured by Kyoto Electronics Manufacturing Co., Ltd.

The decomposition product solution obtained by the depolymerization reaction generally comprises BHET as a main solute (decomposition product) and EG as a main solvent, contains, as an accessory solute, DEG ester that is contained in the terephthalic polyester (PET in particular) which is a raw material or that is produced by a side reaction upon depolymerization, and can also contain, as other solute components, an oligomer of BHET and mono(2-hydroxyethyl)terephthalate (hereinafter may be abbreviated as "MHET") and, as non-solute components, free DEG caused by a DEG component contained in the raw material terephthalic polyester and a DEG component produced by a side reaction upon depolymerization. Further, when the terephthalic polyester (PET in particular) as a raw material contains a gas barrier agent, the decomposition product solution contains a gas barrier agent component, and the solution can also contain a catalyst used in the depolymerization (such as an alkali metal compound), a catalyst used in the polycondensation reaction of the polyester (such as an antimony compound or a germanium compound), a stabilizer (such as a phosphorus compound), a colorant (such as phthalocyanine dye, anthraquinone dye, monoazo dye, iron oxide or carbon black), and impurity ions derived from various stains which are difficult to expect.

The EG solution containing crude BHET in the first method of the present invention is preferably a solution showing a solid (solute) content at the time of the impurity-removing treatment or crystallization treatment of preferably 5 to 40 wt %, more preferably 10 to 30 wt %, particularly preferably 17 to 23 wt %. When the solid content of the EG solution obtained by the depolymerization reaction (decomposition reaction) fails to satisfy the above range, it is preferable to adjust the solid content by use of EG.

It is preferable that the EG solution containing crude BHET in the first method of the present invention be passed through an activated carbon layer at a temperature at which the solutes are not precipitated (e.g., a temperature higher than 50° C.) and which is not higher than 100° C., preferably a temperature of 70 to 90° C., before subjected to the crystallization treatment so as to be decolorized and the EG solution be further brought into contact with the cation exchanger and then with anion exchanger so as to reduce the contents of coloring components, cations and anions.

The electric conductivity of the EG solution is preferably adjusted to 0.2 to 0.6 μS/cm, more preferably 0.2 to 0.5 μS/cm, by the above ion exchange treatment. Further, the pH of the EG solution is preferably 2.5 to 7.0, more preferably 3.0 to 5.0. To render the electric conductivity lower than 0.2 μS/cm, the duration of the ion exchange treatment must be increased. This increases the side reaction and makes the pH smaller than 2.5, i.e., makes the solution closer to the acidic side undesirably. Meanwhile, when the electric conductivity is higher than 0.6 μS/cm, the growth of precipitated particles in the crystallization treatment is inhibited. Thus, the precipitated particles are small, resulting in a decrease in yield in filtration and a reduction in quality due to residual impurities undesirably. The electric conductivity can be measured by directly applying an electric conductivity meter 873CC of FOX BOLO CO., LTD. to the sample.

The deionization treatment of the EG solution can be carried out by, for example, passing the EG solution through a layer of ion exchangers filled in a column so as to make them contact with each other. When the above EG solution is a suspension, blockages occur in the ion-exchanger-filled layer, whereby inadequate passing of the EG solution or partial flow by passing-resisting spots occurs, so that a stable deionization treatment is difficult to carry out. Accordingly, contact of the cation and anion exchangers with the EG solution is preferably carried out with the EG solution kept at a temperature which is not higher than the maximum working temperatures of the ion exchange resins and at which crystals of BHET are not separated out of the EG solution, after solid impurities (such as fine particles) of at least 1 μm in size are removed from the EG solution as required.

In general, the maximum working temperature of the cation exchanger is higher than that of the anion exchanger. Thus, it is preferred that the EG solution be cooled at least to the maximum working temperature of the anion exchanger after the cation exchange treatment or the cation and anion exchange treatments be carried out at the maximum working temperature of the anion exchanger or a lower temperature. The proportion of cations contained in ion impurities is generally significantly higher than that of anions in the impurities. Further, the EG solution after the cation exchange treatment is significantly shifted to the acidic side, and this leads to side reactions (an ester interchange reaction between BHET and DEG and a hydrolysis reaction of BHET) in the EG solution. Consequently, for the purpose of pH adjustment as well, the anion exchange treatment is preferably carried out without allowing a long time to pass after the cation exchange treatment.

In the present invention, the EG solution is caused to contact with the cation exchanger for a residence time of 3 to 30 minutes, preferably 3 to 15 minutes. Further, contact of the decomposition product solution with the cation exchanger is preferably carried out at a space velocity of 1 to 12 hr$^{-1}$, more preferably at a space velocity of 4 to 9 hr$^{-1}$. When the residence time is less than 3 minutes, a sufficient cation exchange treatment cannot be carried out, resulting in production of an oligomer from BHET by catalysis of residual cations. On the other hand, when the residence time exceeds 30 minutes, the amount of BHET converted into DEG ester by the ester interchange reaction becomes higher than a permissible value undesirably.

Further, after brought into contact with the cation exchanger, the EG solution must be in contact with the anion exchanger over a period ranging from 3 seconds to 10 minutes, preferably 3 seconds to 5 minutes, more preferably 3 seconds to 3 minutes. Thereby, the above ester interchange reaction and hydrolysis reaction can be inhibited.

The cation and anion exchangers can take a general form. For example, they may take the form of particles, chains or fibers or may be amorphous. When they are in the form of particles, the exchangers and the EG solution can be brought into contact with each other by, for example, filling the exchangers in a column and passing the above EG solution through the column.

The cation exchanger is preferably a strongly acidic cation exchange resin, and the anion exchanger is preferably a mixture of a weakly basic anion exchange resin and a strongly acidic cation exchange resin. A cation exchange functional group of the cation exchange resin may be —$SO_3H$ or —COOH, for example. Further, as the cation exchange resin, commercially available ones such as DIAION SK1B, SK104, SK110, SK112 and SK116 (products of MITSUBISHI CHEMICAL CORPORATION) and AMBERLITE IR120B, IR120BN, IR124 and 200CT (products of Rohm & Haas Co. Ltd.) can be used. In these commercial products, ion exchange functional groups are generally stabilized as salts such as sodium salts. Thus, to use these products, the above salts are generally converted into such acid groups as described above.

The anion exchange resin is preferably one having —$NR_2$, —$NH(C_2H_4NH)_nH$, —$N^+R_3(OH)^-$ (R: alkyl group) or the like as an anion exchange functional group. As these anion exchange resins, commercially available ones such as DIAION WA10, WA20, WA21J and WA30 (products of MITSUBISHI CHEMICAL CORPORATION) and AMBERLITE IRA400J, IRA67, IRA96SB and XE583 (products of Rohm & Haas Co. Ltd.) can be used. Of these commercial products, strongly basic anion exchange resins have ion exchange functional groups which are generally stabilized as groups having not hydroxide ions $OH^-$ but halogen anions. Thus, to use these strongly basic anion exchange resins, the ion exchange functional groups are generally converted into groups having hydroxyl group anions as described above. Of these, a weakly basic anion exchange resin having a primary, secondary or tertiary amine as an exchange functional group is preferred.

The above primary, secondary and tertiary amine type anion exchange resins have ion exchangeable —$N^+R_3(OH)^-$ for the first time when they become neutral or acidic (preferably acidic). Thus, it is preferable to use the resins in the form of a mixed bed of the weakly basic anion exchange resin and a strongly acidic cation exchange resin. The mixing ratio (volume ratio) of the weakly basic anion exchange resin to the strongly acidic cation exchange resin is 1:3 to 5:1, preferably 1:2 to 3:1.

In the above anion exchange treatment, the EG solution is in contact with the anion exchanger for a residence time of 3 to 60 minutes, preferably 3 to 40 minutes. Further, contact of the EG solution with the anion exchanger is preferably carried out at a space velocity of 0.5 to 10 hr$^{-1}$, more preferably at a space velocity of 1 to 8 hr$^{-1}$.

In the first method of the present invention, it is preferable to confirm that the ion exchange treatment of the EG solution is appropriate, by measuring the electric conductivity and pH of the EG solution and checking whether these properties are within the above ranges. When it is determined that the treatment is inappropriate, it is preferable to carry out the ion exchange treatment again. The content of DEG ester in the EG solution (to be subjected to the crystallization treatment) after the ion exchange treatment is preferably not higher than 8 wt %, more preferably 1 to 8 wt %, particularly preferably 1 to 6 wt %, based on all solutes.

(Crystallization Step)

The EG solution containing crude BHET in the first method of the present invention is heated to a temperature of at least saturation solubility (preferably 50 to 100° C., more preferably 70 to 90° C.) so as to dissolve solutes completely, cooled to temperatures ranging from 15 to 30° C., preferably 15 to 27° C., and retained in the temperature range for at least 1 hour, preferably 1 to 12 hours, more preferably 2 to 10 hours, particularly preferably 3 to 8 hours so as to precipitate BHET such that the precipitate has an average particle diameter of 40 to 200 µm (measured by use of SALD-200V ER of Shimadzu Corporation with the solution diluted to 10 times by EG).

For example, it is preferable that the EG solution be cooled from a temperature of at least saturation solubility to a given temperature within the range of 15 to 30° C. and kept at the temperature for a given time. After the EG solution is cooled to the given temperature, the temperature of the EG solution may be somewhat increased or decreased within the temperature range of 15 to 30° C. Counting of the given time starts when the temperature of the EG solution reaches 30° C.

By keeping the temperature of the EG solution within the temperature range, the content of a DEG component in the precipitate can be reduced. When the temperature of the EG solution is lower than 15° C., the amount of precipitated DEG ester increases, while when it is higher than 30° C., the solubility of BHET increases, thereby causing a reduction in yield in the crystallization treatment undesirably.

When the EG solution is cooled from a temperature of at least saturation solubility by batch crystallization, the solution is preferably cooled slowly at a cooling rate of 0.1 to 0.5° C./min, preferably 0.1 to 0.3° C./min. With the cooling rate, excessive cooling only in a portion of the solution can be prevented, and the content of the DEG component in the precipitate can be reduced. Meanwhile, in the case of continuous crystallization, it is preferable that an EG solution containing crude BHET of at least saturation solubility be added to and mixed with an EG solution which has been cooled to temperatures ranging from 15 to 30° C. in advance and containing a precipitate and the mixed solution be then cooled.

In the first method of the present invention, by cooling the above ion-exchanged EG solution and keeping the solution at temperatures ranging from 15 to 30° C., preferably 15 to 27° C., crystals of BHET are grown, thereby facilitating solid-liquid separation. As the crystallization temperature lowers, the content of solids in a filtrate decreases and the amount of a cake to be crystallized increases. However, since the EG solution contains DEG ester and, in some cases, a gas barrier agent component, lowering the crystallization temperature causes a problem that crystallization of the DEG ester and gas barrier agent component also proceeds along with crystallization of BHET, thereby lowering the purity of BHET in the cake.

Meanwhile, an increase in the crystallization temperature causes a problem that the crystallization of BHET does not proceed and the solubility of BHET increases, whereby a target yield cannot be attained. Temperature optimization according to the properties of the EG solution is required.

By the crystallization treatment in the first method of the present invention, the sizes of precipitated BHET crystals can be adjusted so that they can be filtered efficiently, and the crystallization of the DEG ester and gas barrier agent component can be minimized. Consequently, in solid-liquid separation after the crystallization, the DEG ester, free DEG and the gas barrier agent component can be left primarily in the filtrate, and the contents of the DEG ester and gas barrier agent component in a filtered cake can be reduced. Further, by the crystallization treatment, coloring substances remaining in the starting material can be separated from the precipitated BHET crystals.

(Solid-Liquid Separation Step)

In the first method of the present invention, solid-liquid separation following the crystallization treatment is carried out with a temperature at the time of the crystallization treatment, i.e., a temperature within a range of 15 to 30° C. maintained. The precipitate after the crystallization treatment is preferably subjected to the solid-liquid separation by a filtration method. Further, the precipitate is preferably filtered out by means of a filter press using a filter fabric having an air permeability of 3 to 30 cm$^3$/min·cm$^2$. When the air permeability of the filter fabric is smaller than 3 cm$^3$/min·cm$^2$, the fabric is liable to have clogging, thereby lowering processing efficiency. Further, the content of a liquid in the filtered cake increases, and impurities in the cake increase. Meanwhile, when the air permeability is larger than 30 cm$^3$/min·cm$^2$, the meshes of the filter fabric are so large that fine particles are fallen into the filtrate undesirably. By the filtration treatment, a filtered cake having a solid content of 40 to 85 wt %, particularly 50 to 80 wt %, can be obtained.

When the precipitate (e.g., the filtered cake) having undergone solid-liquid separation in the first method of the present invention is further subjected to a distillation step, it can be used as a raw material for producing a high-quality polyester again. According to the results of studies made by the present inventors, the distillation efficiency and product quality of BHET is affected by impurities (such as DEG ester) contained in the raw material to be subjected to the distillation step. Thus, by subjecting a raw material which is the precipitate obtained in the first method of the present invention and contains small amounts of impurities, particularly DEG ester and a gas barrier agent component, to the distillation step, the desired objects can be achieved.

Next, the second method of the present invention will be described.

(Starting Material)

An EG solution containing crude BHET which is a starting material in the second method of the present invention is not particularly limited as long as the solution has crude BHET which is a solute (solid) dissolved in EG which is a solvent in an amount of 5 to 85 wt %, preferably 10 to 80 wt %, based on the total weight of the solution. Further, the EG solution containing crude BHET includes the EG solution used as the starting material in the above first method and also includes a solution obtained by subjecting the EG solution to a concentration treatment or crystallization treatment (preferably the crystallization treatment in the first method) and then melting a cake separated from the EG solution by filtration, i.e., an EG solution having crude BHET dissolved in EG in an amount of 40 to 85 wt %, preferably 50 to 80 wt %, based on the total weight of the solution. More specifically, when the starting material is a solution other than a concentrated solution or a filtered cake, the amount of crude BHET is preferably 5 to 40 wt %, more preferably 10 to 40 wt %. Meanwhile, when the starting material is a concentrated solution or a filtered cake, the amount of crude BHET is preferably 40 to 85 wt %, more preferably 50 to 80 wt %.

To the EG solution containing crude BHET which is the starting material in the second method of the present invention, descriptions of the EG solution used as the starting material in the first method and the filtered cake obtained in the first method other than a description of the solid (solute) content can be directly applied.

Therefore, it is to be understood that what has been described with respect to the starting material of the first method is basically included in a description of the starting material of the second method.

To be more specific about the above EG solution as the starting material, it contains crude BHET as a solute and EG as a solvent. Although crude BHET which is a solute most preferably comprise BHET alone, it generally contains, in addition to BHET, at least one solute such as MHET, 1,4-CHDM, bis(2-hydroxyethyl)isophthalate (hereinafter may be abbreviated as "BHEI"), DEG ester or an oligomer (polymerization degree: 2 to 20). Further, the crude BHET preferably contains no gas barrier agent component.

Further, BHET preferably constitutes at least 70 wt %, more preferably at least 80 wt % of the crude BHET from the viewpoint of an improvement in recovery rate of BHET. Further, the content of DEG ester as an impurity component in the crude BHET is not higher than 8 wt %, preferably 1 to 8 wt %, more preferably 1 to 6 wt %. When the content of the DEG ester is higher than 8 wt %, BHET of target quality cannot be obtained at the time of purification by distillation undesirably. Similarly, the content of an oligomer as an impurity component is preferably not higher than 15 wt %, more preferably not higher than 10 wt %. When the content of the oligomer in the starting material is higher than 15 wt %, BHET of target quality cannot be obtained at the time of purification by distillation undesirably. Further, it is needless to say that the total content of these impurity components and BHET does not exceed 100 wt %.

The solvent most preferably comprises EG alone. In general, however, it contains, in addition to EG, at least one impurity component such as free DEG or water. The content of EG in the solvent is preferably not lower than 95 wt %, more preferably not lower than 98 wt %. When the content of the EG is lower than 95 wt %, side reactions caused by impurity components other than EG are liable to occur undesirably. Further, the content of free DEG in the solvent is preferably not higher than 3 wt %, more preferably not higher than 2 wt %. When the content of the free DEG is higher than 3 wt %, DEG ester is liable to be produced by a side reaction undesirably.

(Distillation Step)

An evaporation step in the second method of the present invention comprises a first evaporation step and a second evaporation step. The first evaporation step is a step of evaporating low-boiling-point components (EG, water, free DEG, and the like) in the starting material by use of a first evaporator so as to obtain a first melt solution. The second evaporation step is a step of evaporating low-boiling-point components (EG, free DEG, and the like) in the first melt solution by use of a second evaporator so as to obtain a second melt solution. The low-boiling-point components refer to components (compounds) having a lower boiling point than BHET, such as water, EG and free DEG. An EG solution to be supplied to the first evaporation step is preferably heated at temperatures at which solutes are not precipitated (e.g., temperatures higher than 50° C.) and which are not higher than 100° C., preferably temperatures ranging from 70 to 90° C., when the amount of crude BHET is 5 to 40 wt %,. Meanwhile, when the amount of crude BHET is 40 to 85 wt %, the EG solution is preferably heated at temperatures at which crude BHET is molten but side reactions hardly occur, i.e., 120° C. or lower, more preferably 70 to 120° C., particularly preferably 80 to 120° C.

These first and second evaporators are preferably an evaporator (i.e., a falling-thin-film type evaporator) having heating means for evaporating low-boiling-point components (EG, free DEG, and the like) while causing the starting material or melt solution to fall in the form of a film. This device has an advantage that the low-boiling-point components can be evaporated merely by exposing the solution to high temperatures for a short time (that is, with a short thermal history). Thereby, by-production of DEG from EG can be suppressed. Further, these evaporators also have vacuum means capable of vacuum evaporation.

(First Evaporation Step)

The first evaporation step in the second method of the present invention is preferably carried out at a temperature of 130 to 170° C., preferably 140 to 160° C., and a pressure of 300 to 1,000 Pa, preferably 300 to 700 Pa. The temperature is the temperature of a heating surface, and the pressure is pressure near the heating surface. When the first evaporation treatment is carried out at a temperature lower than 130° C., it takes a long time to evaporate low-boiling-point components (EG, free DEG, and the like) to preferred concentrations, so that production of an oligomer from BHET proceeds undesirably. Meanwhile, when the first evaporation treatment is carried out at a temperature higher than 170° C., DEG is by-produced from EG by a thermal history due to the high temperature, and DEG ester is further by-produced by a reaction between DEG and BHET undesirably. Further, when the first evaporation treatment is carried out at a pressure lower than 300 Pa, solutes (such as BHET) entrain evaporating low-boiling-point components (EG, free DEG, and the like) undesirably. Meanwhile, when the first evaporation treatment is carried out at a pressure higher than 1,000 Pa, it takes a long time to evaporate low-boiling-point components (EG, free DEG, and the like) to preferred concentrations, so that production of an oligomer from BHET proceeds undesirably. If one of the temperature and the pressure is out of the above ranges, an undesirable result is produced.

In the first evaporation step, the solvents (EG, water, DEG, and the like) are evaporated such that the total content of EG and free DEG in the first melt solution obtained is 3 to 10 wt %, preferably 3 to 6 wt %. This treatment time (time in which the solution is in contact with the heating means) is preferably 1 second to 2 minutes, more preferably 1 second to 1 minute.

The solvents distilled off by this treatment are cooled into a condensate by means of a condenser. The condensate can be directly subjected to a distillation purification treatment (re-purification treatment) so as to be used as solvents again. In the present invention, however, it is preferable that the condensate be used as at least a portion of a cooling medium used in an internal condenser of a molecular still before subjected to the above treatment so as to reduce energy consumption. The temperature of the condensate is preferably 20 to 80° C., more preferably 30 to 50° C.

(Second Evaporation Step)

In the second evaporation step in the second method of the present invention, low-boiling-point components (EG, free DEG, and the like) which could not be evaporated by means of the first evaporator and remain in the first melt solution are evaporated. The second evaporation step is carried out at a temperature of 130 to 170° C., preferably 140 to 160° C., and a pressure of 50 to 250 Pa, preferably 50 to 150 Pa. The temperature is the temperature of a heating surface, and the pressure is pressure near the heating surface. When the second evaporation treatment is carried out at a temperature lower than 130° C., it takes a long time to evaporate low-boiling-point components (EG, free DEG, and the like) to preferred concentrations, so that production of an oligomer from BHET proceeds undesirably. Meanwhile, when the second evaporation treatment is carried out at a temperature higher than 170° C., free DEG is by-produced from EG by a thermal history due to the high temperature, and DEG ester is further by-produced by a reaction between free DEG and BHET undesirably. Further, when the second evaporation treatment is carried out at a pressure lower than 50 Pa, solutes (such as BHET) entrain evaporating low-boiling-point components (EG, free DEG, and the like) undesirably. Meanwhile, when the second evaporation treatment is carried out at a pressure higher than 250 Pa, it takes a long time to evaporate low-boiling-point components (EG, free DEG, and the like) to preferred concentrations, so that production of an oligomer from BHET proceeds undesirably. If one of the temperature and the pressure is out of the above ranges, an undesirable result is produced.

In the second evaporator, the low-boiling-point components are evaporated such that the total content of EG and free DEG contained in the second melt solution obtained is not higher than 0.45 wt %, preferably not higher than 0.40 wt %. When the total content of EG and free DEG in the second melt solution is higher than 0.45 wt %, side reactions such as by-production of DEG and by-production of DEG ester caused by by-produced DEG are liable to occur in the molecular distillation step. The treatment time (time in which the solution is in contact with the heating means) in this step is preferably 1 second to 2 minutes, more preferably 1 second to 1 minute.

The total of the content of free DEG in the first and second condensates evaporated and cooled in the evaporation steps and the content of free DEG in the second melt solution obtained in the evaporation steps is preferably not higher than 2 wt % based on the total amount of the condensates and the second melt solution. In the present invention, production of free DEG can be suppressed and production of DEG ester caused by free DEG can also be suppressed in the evaporation steps. Thus, the content of DEG ester in purified BHET can be rendered low.

Further, the content of an oligomer in the second melt solution is preferably not higher than 15 wt %. That is, in the present invention, production of an oligomer is suppressed in the evaporation steps. As a result, the recovery rate of purified BHET can be increased.

The evaporation step in the second method of the present invention is characterized in that an evaporation operation is performed in two steps. When the evaporation operation is performed only in a single step, the following disadvantages result. That is, if the concentration of solvent in the crude BHET molten solution is to be adjusted to 0.45 wt % or lower only in a single step, the solution must be exposed to harsh evaporation conditions (e.g., temperatures higher than 170° C.), and the amounts of by-produced DEG and a by-produced oligomer become larger than those in the present invention. Further, the size of an evaporator becomes so large that the single-step evaporation operation lacks industrial productivity of BHET in terms of costs.

(Molecular Distillation Step)

The molecular distillation step in the second method of the present invention is a step of subjecting the second melt solution obtained in the above evaporation steps to molecular distillation. The molecular still is a falling-thin-film type molecular still comprising heating means for evaporating a portion of the melt solution while causing the melt solution to fall in the form of a film and an internal condenser which condenses a solute (fraction) evaporated (gasified) by the heating means in a short path.

Further, the molecular still is preferably allowed to use the condensate of the solvents evaporated in the evaporation steps as at least a portion of a cooling medium of the internal condenser. As described above, the condensate is preferably cooled to a temperature of 20 to 80° C., more preferably 30 to 50° C. Thereby, the temperature of the cooling medium after mixed with the condensate can be lowered. The BHET condensation temperature of the internal condenser is preferably 115 to 125° C. Further, to condense BHET evaporated by the above heating means in a short path, the distance between the heating surface of the heating means and the cooling surface of the internal condenser should be kept equal to or lower than the average free path of evaporated BHET.

Distillation by the molecular still in the second method of the present invention is carried out at a temperature of 180 to 220° C., preferably 185 to 205° C., and a pressure of not higher than 25 Pa, preferably not higher than 15 Pa. The temperature is the temperature of the heating surface, and the pressure is pressure near the heating surface. When the molecular distillation treatment is carried out at a temperature lower than 180° C., target BHET does not evaporate undesirably. Meanwhile, when the molecular distillation treatment is carried out at a temperature higher than 220° C., DEG ester is by-produced by a reaction between a trace amount of free DEG produced by a thermal history due to the high temperature and BHET undesirably. Further, when the molecular distillation treatment is carried out at a pressure higher than 25 Pa, target BHET flows toward a distillation pot residue before condensed by the internal condenser undesirably, even if the BHET is evaporated. If one of the temperature and the pressure is out of the above ranges, an undesirable result is produced. Time required for this treatment (time in which crude BHET is in contact with the heating means) is preferably 1 second to 1 minute, more preferably 1 second to 50 seconds.

In the molecular still, it is desirable that not all BHET contained in the second melt solution subjected to this distillation treatment be evaporated and BHET be evaporated such that the weight ratio of the fraction to the distillation pot residue be preferably 9:1 to 5:5, more preferably 8:2 to 6:4. For example, when the content of BHET in the second melt solution is 80 to 90 wt %, the weight ratio of the fraction to the distillation pot residue may be 7:3, for example. Thus, by-produced DEG ester whose properties are similar to those of BHET can be caused to remain in the distillation pot residue together with BHET, and a fraction of higher quality, that is, a fraction having a DEG ester content of not higher than 1.5 wt % and an oligomer content of not higher than 1 wt % in the fraction, can be obtained. However, when the required properties of a product are less stringent, the yield can be improved by further increasing the evaporation rate of the fraction.

The distillation pot residue produced in the molecular distillation step contains BHET as a main component. Hence, when it is introduced as a raw material for the above depolymerization of a polyester, it can be used to promote initial depolymerization.

In the above molecular distillation step, as described above, it is preferable to use the condensates obtained in the evaporation steps as at least a portion of the cooling medium for the internal condenser. This treatment will be more specifically described hereinafter. The condensates are subjected to a distillation purification treatment (re-purification treatment) so as to be reused as solvents. However, when the condensates are used as the cooling medium for the internal condenser before subjected to this treatment, the condensates are heated by the evaporation latent heat of steam of BHET and are at elevated temperatures when discharged from the internal condenser. This elevation of the temperatures of the condensates leads to omission of a part of a preheating treatment when the condensates are purified by distillation and contributes to a reduction in energy consumption. Further, the amount of a cooling medium which is newly prepared and used as the cooling medium for the internal condenser can be reduced.

(Distillation Step Diagram)

The method for purifying bis(2-hydroxyethyl)terephthalate in the second method of the present invention will be further described with reference to the drawings. FIG. 1 is a diagram showing a preferred distillation step (a combination of evaporators and a molecular still). In FIG. 1, reference numeral 1 denotes a first evaporator, 2 a condenser, 3 a melt solution transport pump, 4 a second evaporator, 5 a condenser, 6 a melt solution transport pump, 7 a condensate reservoir, 8 a molecular still, 9 an internal condenser, 10 heating means, 11 a product output port, 12 a distillation pot residue output port, 13 a cooling medium circulating tank, and 14 a heating medium tank. The condensers 2 and 5 may be disposed inside or outside the apparatuses. Further, the first evaporator, the second evaporator and the molecular still are connected to vacuum means (not shown) so as to render the insides of the apparatuses vacuum.

In FIG. 1, the first evaporator 1 and the second evaporator 4 are falling-thin-film type evaporators. A starting material (EG solution) is fed to the first evaporator 1, low-boiling-point components (EG, water, free DEG, and the like) evaporated in the apparatus by heating are cooled so as to be condensed into a first condensate in the condenser 2, and the first condensate is reserved in the condensate reservoir 7. A first melt solution is fed to the second evaporator 4 by means of the melt solution transport pump 3, low-boiling-point components (EG, free DEG, and the like) evaporated in the apparatus by heating are cooled so as to be condensed into a second condensate in the condenser 5, and the second condensate is fed to a distillation purification system.

The second melt solution is fed to the molecular still 8 by means of the melt solution transport pump 6, a fraction is evaporated by the heating means 10 in the apparatus 8, and the evaporated fraction is cooled in the internal condenser 9. The fraction cooled in the internal condenser 9 is taken out as products from the product output port 11. A residue other than the fraction is taken out from the distillation pot residue output port 12.

In a preferred embodiment, the condensate from the evaporation steps which is reserved in the condensate reservoir 7 is mixed with a cooling medium from the cooling medium circulating tank 13 so as to be used for cooling in the internal condenser 9, and the (temperature-raised) cooling medium discharged from the condenser 9 is returned to the cooling medium circulating tank 13, and an amount corresponding to the amount of the mixed condensate is separated therefrom. The separated liquid may be fed to the distillation purification treatment (recovery purification) system or may be fed to the heating medium tank 14 which supplies a heating medium to the heating means 10 of the molecular still 8. The heating medium is heated to a desired temperature in the heating medium tank 14. Further, a high-temperature liquid produced in the distillation purification treatment (recovery purification) system may be fed to the heating medium tank 14 and used as a heating medium. Thereby, energy consumption in the distillation method using the evaporators and the molecular still in a multistage manner can be reduced.

Next, the third method of the present invention will be described.

The third method of the present invention is a combination of the above first and second methods. Thus, a description of the third method is basically the same as those of the first and second methods. Hereinafter, the third method will be described briefly, although it is deemed that some characteristics thereof have already been described with respect to the first and second methods.

(Starting Material)

In the third method of the present invention, an EG solution containing crude BHET which is a starting material is the same as the starting material used in the first method of the present invention. Therefore, this EG solution is preferably a solution obtained by depolymerizing a terephthalic polyester with EG and subjecting the polyester to an impurity-removing treatment during or after the depolymerization or a solution obtained by an esterification reaction between terephthalic acid and EG (preferably a deionized solution). These solutions can be prepared in accordance with the method described above with respect to the first method of the present invention. An EG solution containing crude BHET which is obtained by the method is subjected to a crystallization step.

(Crystallization Step)

The EG solution containing crude BHET in the third method of the present invention is subjected to the crystallization step in accordance with the method described with respect to the first method of the present invention. More specifically, the desired object can be achieved by heating the EG solution to a temperature of at least saturation solubility so as to dissolve solutes completely, cooling the solution to temperatures ranging from 15 to 30° C., and keeping the solution within the temperature range for at least 1 hour.

(Solid-Liquid Separation Step)

By subjecting a precipitate after the crystallization treatment in the third method of the present invention to the solid-liquid separation step described with respect to the first method of the present invention, a filtered cake containing BHET as a main component can be obtained. That is, the target filtered cake can be obtained by subjecting the precipitate precipitated by crystallization and containing BHET as a main component to solid-liquid separation with the precipitate kept at crystallization temperatures (15 to 30° C.). The filtered cake is formed into a melt solution so as to be subjected to the subsequent step. It is preferred to heat the filtered cake at such temperatures (e.g., 120° C. or lower, more preferably 70 to 120° C., particularly preferably 80 to 120° C.) that the filtered cake melts but side reactions hardly occur.

(Evaporation Step)

An evaporation step in the third method of the present invention is carried out by use of the above filtered cake as a raw material to be subjected to the evaporation step in accordance with the method described with respect to the second method of the present invention. That is, a melt solution of the above filtered cake is charged into the first evaporator, and low-boiling-point components are evaporated at a temperature of 130 to 170° C. and a pressure of 300 to 1,000 Pa so as to obtain a first melt solution having a total content of EG and free DEG of 3 to 10 wt %. The first melt solution is then charged into the second evaporator, and low-boiling-point components are evaporated at a temperature of 130 to 170° C. and a pressure of 50 to 250 Pa so as to obtain a second melt solution having a total content of EG and free DEG of not higher than 0.45 wt %. By such an evaporation step, the desired object can be achieved.

(Molecular Distillation Step)

A molecular distillation step in the third method of the present invention is carried out by use of the second melt solution obtained in the above evaporation step in accordance with the method described with respect to the second method of the present invention. That is, the target object can be achieved by charging the above second melt solution into the falling-thin-film type molecular still and distilling the solution at a temperature of 180 to 220° C. and a pressure of not higher than 25 Pa.

Thus, according to the present invention, high-quality bis(2-hydroxyethyl)terephthalate can be obtained efficiently by purifying crude bis(2-hydroxyethyl)terephthalate by the above operation. Further, the purified bis(2-hydroxyethyl) terephthalate of the present invention can be polymerized in the presence of a polymerization catalyst so as to produce a polyethylene terephthalate.

EXAMPLES

Hereinafter, the present invention will be further described with reference to Examples. It is needless to say that the present invention shall not be limited by Examples. Further, properties in Examples were measured in the following manner.

1. Separation of Components and Measurement of Amounts Thereof 50 mg of sample was dissolved in chloroform so as to prepare about 1,000 ppm of solution, and a measurement was made by using an ultraviolet visible spectrophotometer as a detector at a measurement wavelength of 240 nm and a silica-60 column of 4.6 mm$^{ID}$×250 mm$^L$ in high-performance liquid chromatography (HPLC) LC-6 of Shimadzu Corporation with a temperature of 40° C., a flow rate of 1.0 ml/mm, an injection rate of 5 μl and dichloromethane/dioxane as a mobile phase.

2. Identification of Solution Components

An LC/MS measurement was made so as to identify peaks of HPLC. The peaks were measured and identified under the same conditions as described above by use of SX-102A of JEOL.

3. Optical Density of Sample 50 mg of sample was dissolved in methanol so as to prepare a 10 wt % methanol solution. The absorbance at 380 nm of this solution was measured by means of UVmini-1240 (product of Shimadzu Corporation) with a cell length of 20 mm and blanks zero-point corrected by use of methanol.

4. Electric Conductivity

Electric conductivity was measured continuously by use of electric conductivity meter 873CC of FOX BOLO CO., LTD.

5. Water Content

A water content was measured by use of an MK-SS type Karl Fischer moisture meter manufactured by Kyoto Electronics Manufacturing Co., Ltd.

6. pH

The pH of an ethylene glycol solution having a solid content at 80° C. of 20 wt % was measured by "JISZ8802".

7. Average Particle Diameter of Precipitate

The average particle diameter of a precipitate was measured by use of SALD-200V ER of Shimadzu Corporation by diluting a crystallization solution to 10 times with EG.

Example 1

(Preparation of Starting Material)

(Preliminary Depolymerization)

57 kg of flakes with an average size of 8 mm×8 mm which had been obtained by crushing and adjusting post-consumer PET bottles (bottles made of a polyethylene terephthalate) mixed with 10 wt % of colored PET bottles and 25 kg of mixture of bis(2-hydroxyethyl)terephthalate(BHET) and an oligomer thereof were charged into an 800-liter autoclave equipped with a stirrer and subjected to preliminary depolymerization under normal pressure at 250° C.

(Depolymerization)

Then, to the preliminary depolymerization product, 418 kg of ethylene glycol (EG) and 0.23 kg of sodium hydroxide as a depolymerization catalyst were added, and the depolymerization reaction was further promoted at a pressure of 0.15 MPa and a temperature of 220° C. so as to obtain 500 kg of depolymerization reaction solution.

(Removal of Solid Foreign Materials)

This solution was cooled to 180° C., solid foreign materials (caps, labels, and the like) which had not been decomposed in the depolymerization reaction were removed by a 60-mesh line strainer, and the resulting solution was transported to an 800-liter cooling bath.

(Decolorization Treatment)

The temperature of the reaction solution in the cooling bath was lowered to 80° C., and solid foreign materials such as pigments and fine particles having a particle diameter of not smaller than 1 μm were removed by a cartridge filter. Then, the reaction solution was passed through a decolorization column filled with activated carbon (105 kg of "DIAHOPE008" of Mitsubishi Chemical Corporation) at a space velocity of 0.57 hr$^{-1}$ so as to be decolorized.

(Cation Exchange Treatment)

Then, the resulting solution was passed through a cation-removing column filled with a cation exchanger (25 liters of cation exchange resin "AMBERLITE IR-120B" of Rohm & Haas Co., Ltd.) at a temperature of 80° C. and a space velocity of 4.8 hr$^{-1}$ so as to be subjected to a cation exchange treatment.

(Anion Exchange Treatment)

Thereafter, the resulting solution was passed through a connected pipe within 30 seconds and then passed through an anion-removing column filled with an anion exchanger (mixture of 30 liters of anion exchange resin "AMBERLITE IRA96SB" and 30 liters of cation exchange resin "AMBERLITE IR-120B" of Rohm & Haas Co., Ltd.) at a temperature of 80° C. and a space velocity of 2 hr$^{-1}$ so as to be subjected to an anion exchange treatment. Thereby, the deionization treatment was completed.

The pH of the reaction solution was 5.2 before the cation exchange treatment, 1.8 after the cation exchange treatment, and 4.9 after the anion exchange treatment. Further, the electric conductivity of the reaction solution was 537 μS/cm before the cation exchange treatment and 0.4 μS/cm after the anion exchange treatment. Further, the solid (solute) concentration of the reaction solution after the anion exchange treatment was 19.5 wt %. Further, the content of 2-hydroxyethyl[2-(2-hydroxyethoxy)ethyl]terephthalate (DEG ester) in the solid (solute) of the reaction solution was 4.0 wt %.

(Crystallization Step)

The above deionized solution was cooled in a crystallization bath from 80° C. to 25° C. at a rate of 0.2° C./min and kept at 25° C. for 5 hours so as to be crystallized. The average particle diameter of a precipitate was 60 μm.

(Solid-Liquid Separation Step)

Thereafter, the resulting solution was subjected to solid-liquid separation by use of a filter press using a filter fabric having an air permeability of 5 cm$^3$/min·cm$^2$ while kept at 25° C. so as to obtain 145 kg (recovery rate: 29 wt %) of cake containing 60 wt % of crude BHET and 355 kg of (recovery rate: 71 wt %) of filtrate having a solid content of 3.5 wt %. The content of DEG ester in the cake was 1.8 wt %.

Example 2

(Preparation of Starting Material)

A starting material was prepared in the same manner as in Example 1.

(Crystallization Step)

The crystallization step of Example 1 was repeated except that the crystallization temperature was 15° C. The average particle diameter of a precipitate was 61 μm.

(Solid-Liquid Separation Step)

A cake was obtained in the same manner as in Example 1.

As a result, 150 kg (recovery rate: 30 wt %) of the cake containing 61 wt % of crude BHET and 350 kg of (recovery rate: 70 wt %) of filtrate having a solid content of 2.5 wt % were obtained. The content of DEG ester in the cake was 2.3 wt %.

From these facts, an improvement in crystallization efficiency can be generally expected by lowering the crystallization temperature, and in the present invention as well, the tendency can be seen in the solid contents in the filtrate and cake. At the same time, it was also found that the content of DEG ester which was a content other than BHET in the cake increased as solubility to EG was lowered. From this result, it was disclosed that to obtain BHET of higher purity, a higher crystallization temperature is better as long as crystals of BHET could be obtained.

Comparative Example 1

(Preparation of Starting Material)

A starting material was prepared in the same manner as in Example 1.

(Crystallization Step)

A cake was obtained in the same manner as in Example 1 except that the crystallization temperature was 5° C. The average particle diameter of a precipitate was 62 μm.

(Solid-Liquid Separation Step)

A cake was obtained in the same manner as in Example 1.

As a result, 155 kg (recovery rate: 31 wt %) of the cake containing 62 wt % of crude BHET and 345 kg of (recovery rate: 71 wt %) of filtrate having a solid content of 1.7 wt % were obtained. Although an effect caused by a decrease in the temperature was clearly recognized in terms of contents, the content of DEG ester in the cake reached 3.0 wt %.

Comparative Example 2

(Preparation of Starting Material)

A starting material was prepared in the same manner as in Example 1.

(Crystallization Step)

The crystallization step of Example 1 was repeated except that the crystallization temperature was 35° C. As a result, a satisfactory crystallization result could not be obtained, the content of solids in a filtrate reached 7 wt %, and the subsequent step could not be carried out.

Table 1 shows the yields of solids and the contents of DEG esters in the crystallization steps of Examples 1 and 2 and Comparative Example 1.

TABLE 1

| | Properties of Crystallization Solution | Conditions for Crystallization | Properties of Cake | | | Properties of Filtrate | | Total Solid |
|---|---|---|---|---|---|---|---|---|
| | Content of DEG Component (wt %) | Temperature (° C.) | Recovery Rate (wt %) | Solid Content (wt %) | Content of DEG Component (wt %) | Recovery Rate (wt %) | Solid Content (wt %) | Content (wt %) |
| Ex. 1 | 4.0 | 25 | 29 | 60 | 1.8 | 71 | 3.5 | 19.9 |
| Ex. 2 | 4.0 | 15 | 30 | 61 | 2.3 | 70 | 2.5 | 20.1 |
| C. Ex. 1 | 4.0 | 05 | 31 | 62 | 3.0 | 69 | 1.7 | 20.0 |

Ex.: Example,
C. Ex.: Comparative Example

Example 3

(Preparation of Starting Material)

A starting material was prepared in the same manner as in Example 1. The obtained deionized solution was used as a starting material for purification in the evaporation steps shown in FIG. 1.

(First Evaporation Step)

The starting material was fed to the first falling-thin-film type evaporator at a feed rate of 138 kg/hr so as to evaporate low-boiling-point components at a temperature of 150° C. and a pressure of 500 Pa. The evaporation treatment time was 3.6 hours. The amount of a first condensate produced by cooling the low-boiling-point components was 109kg/hr. The amount of a produced first melt solution was 29 kg/hr.

The total content of EG and free DEG and the content of an oligomer in the first melt solution are shown in Table 2.

(Second Evaporation Step)

Then, the first melt solution was fed to the second falling-thin-film type evaporator at a feed rate of 29 kg/hr so as to evaporate remaining low-boiling-point components at a temperature of 150° C. and a pressure of 80 Pa. The evaporation treatment time was 3.7 hours. The amount of a second condensate produced by cooling the low-boiling-point components was 2 kg/hr. The amount of a produced second melt solution was 27 kg/hr.

The content of free DEG in the first and second condensates and the second melt solution, and the total content of EG and free DEG and the content of an oligomer in the second melt solution are shown in Table 2.

(Molecular Distillation Step)

The second melt solution was fed to the falling-thin-film type molecular still at a feed rate of 27 kg/hr, and molecular distillation was carried out at a temperature of 195° C. and a pressure of 13 Pa so as to distill out a fraction such that the weight ratio of the fraction to a distillation pot residue became 7:3. The fraction was distilled out at a rate of 19 kg/hr, and time required by the distillation was 3.7 hours. In the molecular distillation, the whole amount of the first condensate obtained in the first evaporation step was used as a portion of a cooling medium for the internal condenser. The results of analysis of the obtained fraction are shown in Table 3.

Example 4

(Preparation of Starting Material)

A starting material was prepared in the same manner as in Example 1.

(Crystallization Step)

A crystallization step was carried out in the same manner as in Example 1. The obtained cake was heated and molten in a nitrogen atmosphere at 100° C. and used as a starting material for purification in the distillation step shown in FIG. 1.

(First Evaporation Step)

The starting material was fed to the first falling-thin-film type evaporator at a feed rate of 50 kg/hr so as to evaporate low-boiling-point components at a temperature of 150° C. and a pressure of 500 Pa. The evaporation treatment time was 2.9 hours. The amount of a first condensate produced by cooling the low-boiling-point components was 18 kg/hr. The amount of a produced first melt solution was 32 kg/hr.

The total content of EG and free DEG and the content of an oligomer in the first melt solution are shown in Table 2.

(Second Evaporation Step)

Then, the first melt solution was fed to the second falling-thin-film type evaporator at a feed rate of 32 kg/hr so as to evaporate remaining low-boiling-point components at a temperature of 150° C. and a pressure of 80 Pa. The evaporation treatment time was 2.9 hours. The amount of a second condensate produced by cooling the low-boiling-point components was 2 kg/hr. The amount of a produced second melt solution was 30 kg/hr.

The content of free DEG in the first and second condensates and the second melt solution, and the total content of EG and free DEG and the content of an oligomer in the second melt solution are shown in Table 2.

(Molecular Distillation Step)

The second melt solution was fed to the falling-thin-film type molecular still at a feed rate of 30 kg/hr, and molecular distillation was carried out at a temperature of 195° C. and a pressure of 13 Pa so as to distill out a fraction such that the weight ratio of the fraction to a distillation pot residue became 7:3. The fraction was distilled out at a rate of 21 kg/hr, and time required by the distillation was 2.9 hours. The results of analysis of the obtained fraction are shown in Table 3.

Comparative Example 3

(Preparation of Starting Material)

A starting material was prepared in the same manner as in Example 1.

(Evaporation Step)

A first evaporation step was carried out in the following manner, and a second evaporation step was not carried out. That is, the starting material was fed to the evaporator at a feed rate of 25 kg/hr so as to evaporate low-boiling-point components at a temperature of 150° C. and a pressure of 500 Pa. The evaporation treatment time was 20 hours. The amount of a condensate produced by cooling the low-boiling-point components was 20 kg/hr. The amount of a produced melt solution was 5 kg/hr.

The content of free DEG in the first condensate and the first melt solution, and the total content of EG and free DEG and the content of an oligomer in the first melt solution are shown in Table 2.

(Molecular Distillation Step)

The first melt solution obtained by the above procedure was fed to the falling-thin-film type molecular still at a feed rate of 5 kg/hr, and molecular distillation was carried out at a temperature of 190° C. and a pressure of 13 Pa so as to distill out a fraction such that the weight ratio of the fraction to a distillation pot residue became 7:3. The fraction was distilled out at a rate of 3.5 kg/hr, and time required by the distillation was 20.1 hours. The results of analysis of the obtained fraction are shown in Table 3.

As can be understood from Table 3, the evaporation treatment was carried out only in the first evaporator and evaporation of the solvents was performed for a long time in the presence of a large amount of EG which was a low-boiling-point component, the content of DEG ester in the fraction was 1.9 wt %.

Comparative Example 4

(Preparation of Starting Material)

A starting material was prepared in the same manner as in Example 1.

(Evaporation Step)

A first evaporation step was carried out in the same manner as in Example 1, and a second evaporation step was not carried out.

The content of free DEG in the first condensate and the first melt solution, and the total content of EG and free DEG and the content of an oligomer in the first melt solution are shown in Table 2.

(Molecular Distillation Step)

The first melt solution obtained by the above procedure was fed to the falling-thin-film type molecular still at a feed rate of 29 kg/hr, and molecular distillation was carried out at a temperature of 197° C. and a pressure of 13 Pa so as to distill out a fraction such that the weight ratio of the fraction to a distillation pot residue became 7:3. The fraction was distilled out at a rate of 20.3 kg/hr, and time required by the distillation was 3.6 hours. The results of analysis of the obtained fraction are shown in Table 3.

In Comparative Example 4, the molecular distillation treatment was carried out with 5.1 wt % of low-boiling-point components remaining. Accordingly, solutes such as BHET entrained evaporated solvents and stuck on the internal wall of the condenser situated before the vacuum means, thereby making it difficult to perform a stable molecular distillation operation.

TABLE 2

Results of Analysis of Condensates and Melt Solutions in Evaporation Steps

|  | Ex. 3 | Ex. 4 | C. Ex. 3 | C. Ex. 4 |
|---|---|---|---|---|
| Content of Free DEG in Condensate(s) and Melt Solution in Evaporation Steps (wt %)[1] | 1.4 | 1.2 | 3.1 | 1.4 |
| Content of EG and Free DEG in First Melt Solution (wt %) | 5.1 | 5.1 | 0.4 | 5.1 |
| Content of Oligomer in First Melt Solution (wt %) | 11.1 | 11.1 | 20.4 | 11.1 |
| Content of EG and Free DEG in Second Melt Solution (wt %) | 0.3 | 0.3 | — | — |
| Content of Oligomer in Second Melt Solution (wt %) | 12.0 | 12.0 | — | — |

Ex.: Example,
C. Ex.: Comparative Example
[1])Example 3 . . . Content of Free DEG in First and Second Condensates and Second Melt Solution Comparative Examples 3 and 4 . . . Content of Free DEG in First Condensate and First Melt Solution
DEG: diethylene glycol
EG: ethylene glycol

TABLE 3

Results of Analysis of Fractions by Molecular Distillation

| Quality of Purified BHET after Molecular Distillation | Ex. 3 | Ex. 4 | C. Ex. 3 | C. Ex. 4 |
|---|---|---|---|---|
| Yield of Purified BHET (kg) | 70 | 61 | 70 | 61 |
| Optical Density (380 nm) | 0.002 | 0.000 | 0.005 | 0.007 |
| Content of BHET (wt %) | 99.0 | 99.2 | 96.8 | 97.0 |
| Content of DEG Ester (wt %) | 0.7 | 0.5 | 1.9 | 2.5 |
| Content of Oligomer (wt %) | 0.2 | 0.2 | 1.2 | 0.3 |
| Others (wt %) | 0.1 | 0.1 | 0.1 | 0.2 |

Ex.: Example,
C. Ex.: Comparative Example
BHET . . . bis(2-hydroxyethyl)terephthalate
DEG ester . . . 2-hydroxyethyl[2-(2-hydroxyethoxy)ethyl]terephthalate
MHET . . . mono(2-hydroxyethyl)terephthalate Comparative Examples 5 to 12

(Preparation of Starting Material)

Starting materials were prepared in the same manner as in Example 1.

(First Evaporation Step)

The starting materials were fed to the first falling-thin-film type evaporator, and low-boiling-point components were evaporated under evaporation conditions of Table 4 such that the total contents of EG and free DEG in first melt solutions became 5 wt %.

TABLE 4

| | C. Ex. | | | | | | | |
|---|---|---|---|---|---|---|---|---|
| | 5 | 6 | 7 | 8 | 9 | 10 | 11 | 12 |
| Temperature (° C.) | 120 | 120 | 120 | 180 | 180 | 180 | 150 | 150 |
| Pressure (Pa) | 200 | 500 | 2000 | 200 | 500 | 2000 | 200 | 2000 |

TABLE 4-continued

| | C. Ex. | | | | | | | |
|---|---|---|---|---|---|---|---|---|
| | 5 | 6 | 7 | 8 | 9 | 10 | 11 | 12 |
| Evaporation Time (hr) | 4.0 | 4.6 | 5.5 | 2.8 | 3.2 | 3.9 | 3.2 | 4.3 |

C. Ex.: Comparative Example

The total contents of EG and free DEG and the contents of oligomers in the first melt solutions are shown in Table 5.

(Second Evaporation Step)

A second evaporation step was carried out in the same manner as in Example 3. The contents of free DEG in the first and second condensates and the second melt solutions, and the total contents of EG and free DEG and the contents of oligomers in the second melt solutions are shown in Table 5.

(Molecular Distillation Step)

The second melt solutions obtained by the above procedure were fed to the falling-thin-film type molecular still, and fractions were distilled out such that the weight ratio of the fraction to a distillation pot residue became 7:3. The results of analysis of the obtained fractions are shown in Table 6.

In Comparative Examples 5 to 12, the first evaporation step was carried out under various evaporation conditions. It is seen that in all cases, some influence was exerted on the quality or yield of purified BHET.

TABLE 5

Results of Analysis of Condensates and Melt Solutions in Evaporation Step

|  | C. Ex. 5 | C. Ex. 6 | C. Ex. 7 | C. Ex. 8 | C. Ex. 9 | C. Ex. 10 | C. Ex. 11 | C. Ex. 12 |
|---|---|---|---|---|---|---|---|---|
| Content of Free DEG in First and Second Condensates and Second Melt Solution (wt %) | 2.1 | 2.2 | 2.3 | 1.9 | 2.3 | 5.0 | 1.4 | 2.9 |
| Content of EG and Free DEG in First Melt Solution (wt %) | 5.0 | 5.0 | 5.0 | 5.0 | 5.0 | 5.0 | 5.0 | 5.0 |
| Content of Oligomer in First Melt Solution (wt %) | 14.2 | 15.0 | 16.3 | 10.1 | 10.7 | 12.2 | 10.8 | 15.1 |
| Content of EG and Free DEG in Second Melt Solution (wt %) | 0.3 | 0.3 | 0.3 | 0.3 | 0.3 | 0.3 | 0.3 | 0.3 |
| Content of Oligomer in Second Melt Solution (wt %) | 15.1 | 15.9 | 17.2 | 11.0 | 11.6 | 13.1 | 11.7 | 16.0 |

C. Ex.: Comparative Example

TABLE 6

Results of Analysis of Fractions by Molecular Distillation

| Quality of Purified BHET after Molecular Distillation | C. Ex. 5 | C. Ex. 6 | C. Ex. 7 | C. Ex. 8 | C. Ex. 9 | C. Ex. 10 | C. Ex. 11 | C. Ex. 12 |
|---|---|---|---|---|---|---|---|---|
| Yield of Purified BHET (kg) | 68 | 70 | 70 | 50 | 66 | 70 | 63 | 70 |
| Optical Density (380 nm) | 0.005 | 0.005 | 0.006 | 0.004 | 0.006 | 0.008 | 0.003 | 0.007 |
| Content of BHET (wt %) | 97.0 | 96.9 | 96.6 | 98.1 | 97.3 | 96.6 | 98.7 | 96.2 |
| Content of DEG Ester (wt %) | 1.8 | 1.8 | 1.9 | 1.1 | 1.9 | 2.8 | 0.7 | 2.5 |
| Content of Oligomer (wt %) | 1.1 | 1.1 | 1.2 | 0.2 | 0.2 | 0.4 | 0.2 | 1.2 |
| Others (wt %) | 0.1 | 0.2 | 0.1 | 0.4 | 0.4 | 0.2 | 0.4 | 0.1 |

C. Ex.: Comparative Example

Comparative Examples 13 to 20

(Preparation of Starting Material)

Starting materials were prepared in the same manner as in Example 1.

(First Evaporation Step)

A first evaporation step was carried out in the same manner as in Example 3.

(Second Evaporation Step)

First melt solutions were fed to the second falling-thin-film type evaporator, and low-boiling-point components were evaporated under evaporation conditions of Table 7 such that the total contents of EG and free DEG in second melt solutions became 0.3 wt %.

TABLE 7

|  | C. Ex. | | | | | | | |
|---|---|---|---|---|---|---|---|---|
|  | 13 | 14 | 15 | 16 | 17 | 18 | 19 | 20 |
| Temperature (° C.) | 120 | 120 | 120 | 180 | 180 | 180 | 150 | 150 |
| Pressure (Pa) | 40 | 80 | 300 | 40 | 80 | 300 | 40 | 300 |
| Evaporation Time (hr) | 4.2 | 4.7 | 5.6 | 2.9 | 3.3 | 4.1 | 3.4 | 4.4 |

C. Ex.: Comparative Example

The contents of free DEG in the first and second condensates and the second melt solutions, and the total contents of EG and free DEG and the contents of oligomers in the second melt solutions are shown in Table 8.

(Molecular Distillation Step)

The second melt solutions obtained by the above procedure were fed to the falling-thin-film type molecular still, and fractions were distilled out such that the weight ratio of the fraction to a distillation pot residue became 7:3. The results of analysis of the obtained fractions are shown in Table 9.

In Comparative Examples 13 to 20, the second evaporation step was carried out under various evaporation conditions. It is seen that in all cases, some influence was exerted on the quality or yield of purified BHET, as in the case of Comparative Examples 5 to 12.

TABLE 8

Results of Analysis of Condensates and Melt Solutions in Evaporation Steps

|  | C. Ex. 13 | C. Ex. 14 | C. Ex. 15 | C. Ex. 16 | C. Ex. 17 | C. Ex. 18 | C. Ex. 19 | C. Ex. 20 |
|---|---|---|---|---|---|---|---|---|
| Content of Free DEG in First and Second Condensates and Second Melt Solution (wt %) | 1.9 | 2.0 | 2.1 | 1.7 | 2.1 | 2.9 | 1.2 | 2.4 |
| Content of EG and Free DEG in First Melt Solution (wt %) | 5.1 | 5.1 | 5.1 | 5.1 | 5.1 | 5.1 | 5.1 | 5.1 |
| Content of Oligomer in First Melt Solution (wt %) | 11.1 | 11.1 | 11.1 | 11.1 | 11.1 | 11.1 | 11.1 | 11.1 |
| Content of EG and Free DEG in Second Melt Solution (wt %) | 0.3 | 0.3 | 0.3 | 0.3 | 0.3 | 0.3 | 0.3 | 0.3 |
| Content of Oligomer in Second Melt Solution (wt %) | 14.4 | 15.2 | 16.5 | 11.7 | 12.0 | 13.5 | 11.0 | 15.3 |

C. Ex.: Comparative Example

TABLE 9

Results of Analysis of Fractions by Molecular Distillation

| Quality of Purified BHET after Molecular Distillation | C. Ex. 13 | C. Ex. 14 | C. Ex. 15 | C. Ex. 16 | C. Ex. 17 | C. Ex. 18 | C. Ex. 19 | C. Ex. 20 |
|---|---|---|---|---|---|---|---|---|
| Yield of Purified BHET (kg) | 69 | 70 | 70 | 67 | 69 | 70 | 68 | 70 |
| Optical Density (380 nm) | 0.004 | 0.004 | 0.005 | 0.003 | 0.005 | 0.007 | 0.003 | 0.006 |
| Content of BHET (wt %) | 97.6 | 97.6 | 97.0 | 98.3 | 97.6 | 96.9 | 98.8 | 97.3 |
| Content of DEG Ester (wt %) | 1.5 | 1.5 | 1.8 | 1.0 | 1.8 | 2.3 | 0.7 | 1.9 |
| Content of Oligomer (wt %) | 0.5 | 0.6 | 1.1 | 0.2 | 0.2 | 0.4 | 0.2 | 0.6 |
| Others (wt %) | 0.4 | 0.3 | 0.1 | 0.5 | 0.4 | 0.4 | 0.3 | 0.2 |

C. Ex.: Comparative Example

Example 5

(Preparation of Starting Material)

202 kg of crushed flakes of post-consumer PET bottles were preliminarily depolymerized by 118 kg of mixture of BHET and an oligomer thereof under heating at 280° C. Then, 0.96 kg of sodium hydroxide as a depolymerization catalyst and 1,800 kg of EG were added to the preliminary depolymerization product such that the concentration of crude BHET in a depolymerization solution became 20 wt %, and depolymerization was further promoted under heating at 220° C. so as to obtain 2,120 kg of the depolymerization solution containing EG as a solvent.

The temperature of this depolymerization solution was lowered to 80° C., foreign materials and impurities contained were removed in accordance with a known method, the resulting solution was cooled to 25° C., crystallization of BHET was conducted for 5 hours, and slurry containing BHET crystals and EG as a solvent was subjected to a filter press so as to carry out solid-liquid separation. Thereby, 770 kg of crude BHET crystal cake containing 45 wt % of EG was obtained.

The cake obtained by the above procedure was heated to 100° C. in a nitrogen atmosphere so as to be molten and used as a starting material for purification in the evaporation steps shown in FIG. 1. The total concentration of solutes in this starting material was 19.5 wt %. The starting material contained 4.0 wt % of DEG ester based on all solutes and had an electric conductivity of 0.4 µS/cm.

(First Evaporation Step)

The starting material was fed to the first falling-thin-film type evaporator at a feed rate of 50 kg/hr so as to evaporate low-boiling-point components at a temperature of 150° C. and a pressure of 500 Pa. The evaporation treatment time was 15.4 hours. The amount of a first condensate produced by cooling the low-boiling-point components was 21 kg/hr. The amount of a produced first melt solution was 29 kg/hr.

The total content of EG and free DEG and the content of an oligomer in the first melt solution are shown in Table 10.

(Second Evaporation Step)

Then, the first melt solution was fed to the second falling-thin-film type evaporator at a feed rate of 29 kg/hr so as to evaporate remaining low-boiling-point components at a temperature of 150° C. and a pressure of 80 Pa. The evaporation treatment time was 15.9 hours. The amount of a second condensate produced by cooling the low-boiling-point components was 2 kg/hr. The amount of a produced second melt solution was 27 kg/hr.

The content of free DEG in the first and second condensates and the second melt solution, and the total content of EG and free DEG and the content of an oligomer in the second melt solution are shown in Table 10.

(Molecular Distillation Step)

The second melt solution was fed to the falling-thin-film type molecular still at a feed rate of 27 kg/hr, and molecular distillation was carried out at a temperature of 195° C. and a pressure of 13 Pa so as to distill out a fraction such that the weight ratio of the fraction to a distillation pot residue became 7:3. The fraction was distilled out at a rate of 19 kg/hr, and time required by the distillation was 15.7 hours.

In the molecular distillation, the whole amount of the first condensate obtained in the first evaporation step was used as a portion of a cooling medium for the internal condenser. The results of analysis of the obtained fraction are shown in Table 11.

TABLE 10

Results of Analysis of Condensates and Melt Solutions in Evaporation Steps

| | Example 5 |
|---|---|
| Content of Free DEG in Condensates and Melt Solution in Evaporation Steps (wt %) | 1.3 |
| Content of EG and Free DEG in First Melt Solution (wt %) | 5.1 |
| Content of Oligomer in First Melt Solution (wt %) | 11.1 |
| Content of EG and Free DEG in Second Melt Solution (wt %) | 0.3 |
| Content of Oligomer in Second Melt Solution (wt %) | 12.0 |

TABLE 11

Results of Analysis of Fraction by Molecular Distillation

| Quality of Purified BHET after Molecular Distillation | Example 5 |
|---|---|
| Yield of Purified BHET (kg) | 296 |
| Optical Density (380 nm) | 0.000 |
| Content of BHET (wt %) | 99.2 |
| Content of DEG Ester (wt %) | 0.5 |
| Content of Oligomer (wt %) | 0.2 |
| Others (wt %) | 0.1 |

Example 6

(Preparation of Starting Material)

(Preliminary Depolymerization)

57 kg of flakes with an average size of 8 mm×8 mm which had been obtained by crushing and adjusting post-consumer PET bottles (bottles made of a polyethylene terephthalate) mixed with 10 wt % of multilayered colored PET bottles for beers which contained a polymethaxylylene adipamide (Nylon MXD6) as a gas barrier agent and 25 kg of BHET were charged into an 800-liter autoclave equipped with a stirrer and subjected to preliminary depolymerization under heating at normal pressure and a temperature of 250° C.

(Depolymerization)

Then, to the preliminary depolymerization product, 418 kg of EG and 0.23 kg of sodium hydroxide as a depolymerization catalyst were added, and the depolymerization was further promoted at a pressure of 0.13 MPa and a temperature of 220° C. The depolymerization was carried out for 60 minutes with low-boiling-point components such as water distilled off from the top of a rectification column placed on the autoclave so as to obtain 500 kg of depolymerization reaction solution containing EG as a solvent.

(Removal of Solid Foreign Materials)

The reaction solution was cooled to 180° C., undecomposed solid foreign materials (caps, labels, and the like) contained in the reaction solution were removed by use of a 60-mesh line strainer, and the resulting solution was transported to an 800-liter cooling bath.

(Decolorization Treatment)

The solution in the cooling bath was cooled to 80° C., and foreign materials such as pigments and fine particles having a particle diameter of not smaller than 1 µm were removed by a filter. Then, the depolymerization reaction solution was passed through a decolorization column filled with activated carbon (105 kg of "DIAHOPE008" of Mitsubishi Chemical Corporation) at a temperature of 80° C. and a space velocity of 0.57 hr$^{-1}$, and foreign materials such as fine particles and fine carbon powder having a particle diameter of not smaller than 1 µm were then removed by a filter.

(Cation Exchange Treatment)

Then, the reaction solution was passed through a cation-removing column filled with a cation exchanger (25 liters of cation exchange resin "AMBERLITE IR-120B" of Rohm & Haas Co., Ltd.) at a temperature of 80° C. and a space velocity of 4.8 hr$^{-1}$ so as to be subjected to a cation exchange treatment.

(Anion Exchange Treatment)

Thereafter, the resulting solution was passed through a connected pipe within 30 seconds and then passed through an anion-removing column filled with an anion exchanger (mixture of 30 liters of anion exchange resin "AMBERLITE IRA96SB" and 30 liters of cation exchange resin "AMBERLITE IR-120B" of Rohm & Haas Co., Ltd.) at a temperature of 80° C. and a space velocity of 2 hr$^{-1}$ so as to be subjected to an anion exchange treatment. Thereby, the deionization treatment was completed.

The pH of the reaction solution was 5.2 before the cation exchange treatment, 1.8 after the cation exchange treatment, and 4.9 after the anion exchange treatment. The electric conductivity of the reaction solution was 537 µS/cm before the cation exchange treatment and 0.4 µS/cm after the anion exchange treatment. Further, the total content of solutes in the reaction solution after the anion exchange treatment was 19.5 wt %, and the content of DEG ester based on all solutes was 4.0 wt %. Further, the content of a gas barrier agent component (component derived from Nylon MXD6) in the solid (solute) was 0.6 wt %.

(Crystallization Step)

The above deionized solution was cooled in a crystallization bath from 80° C. to 25° C. at a rate of 0.2° C./min and kept at 25° C. for 5 hours so as to be crystallized. The average particle diameter of obtained crystals was 60 µm.

(Solid-Liquid Separation Step)

Thereafter, the resulting solution was subjected to solid-liquid separation at 25° C. by use of a filter press using a filter fabric having an air permeability of 5 cm$^3$/min·cm$^2$ so as to obtain 145 kg (recovery rate: 29 wt %) of cake containing 60 wt % of crude BHET. The content of the gas barrier agent component in the cake was 0.1 wt %. The cake obtained by this procedure was heated to 10° C. and molten in a nitrogen atmosphere and used as a starting material for purification in the distillation steps shown in FIG. 1.

(First Evaporation Step)

The starting material was fed to the first falling-thin-film type evaporator at a feed rate of 50 kg/hr so as to evaporate low-boiling-point components at a temperature of 150° C. and a pressure of 500 Pa. The evaporation treatment time was 15.4 hours. The amount of a first condensate produced by cooling the low-boiling-point components was 21 kg/hr. The amount of a produced first melt solution was 29 kg/hr. The total content of EG and free DEG in the first melt solution was 5.0 wt %.

(Second Evaporation Step)

Then, the first melt solution was fed to the second falling-thin-film type evaporator at a feed rate of 29 kg/hr so as to evaporate remaining low-boiling-point components at a temperature of 150° C. and a pressure of 80 Pa. The evaporation treatment time was 15.9 hours. The amount of a second condensate produced by cooling the low-boiling-point components was 2 kg/hr. The amount of a produced second melt solution was 27 kg/hr. The total content of EG and free DEG in the second melt solution was 0.3 wt %.

(Molecular Distillation Step)

The second melt solution was fed to the falling-thin-film type molecular still at a feed rate of 27 kg/hr, and molecular distillation was carried out at a temperature of 195° C. and a pressure of 13 Pa so as to distill out a fraction such that the weight ratio of the fraction to a distillation pot residue became 7:3. The fraction was distilled out at a rate of 19 kg/hr, and time required by the distillation was 15.7 hours. The results of analysis of the obtained fraction are shown in Table 12.

The optical density at 380 nm of the obtained purified BHET was 0.002, and components derived from the gas barrier polymer were not detected. From this result, it was found that even colored PET bottles having a gas barrier property can be recycled by using the method of the present invention.

TABLE 12

Results of Analysis of Fraction by Molecular Distillation

| Quality of Purified BHET after Molecular Distillation | Example 6 |
|---|---|
| Yield of Purified BHET (kg) | 61 |
| Optical Density (380 nm) | 0.002 |
| Content of BHET (wt %) | 99.0 |
| Content of DEG Ester (wt %) | 0.6 |
| Content of Oligomer (wt %) | 0.2 |
| Others (wt %) | 0.2 |
| Gas Barrier Agent Component (wt %) | Not Detected |

EFFECT OF THE INVENTION

As described above, according to the present invention, high-purity BHET can be obtained from an ethylene glycol solution containing crude bis(2-hydroxyethyl)terephthalate, particularly a decomposition product solution (EG solution) which is obtained by decomposing a polyester containing a polyethylene terephthalate as a main component by use of EG and contains bis(2-hydroxyethyl)terephthalate as a main solute and ethylene glycol as a main solvent, while minimizing by-production of impurity components, particularly DEG, DEG ester and an oligomer, during a purification process and by separating a gas barrier agent component as well as these impurity components efficiently.

POSSIBILITY OF INDUSTRIAL UTILIZATION

The purification methods of the present invention are useful in a so-called "chemical recycle" field in which polyethylene terephthalate molded articles, particularly polyethylene terephthalate bottles, are collected and reused.

The invention claimed is:

1. A method of purifying bis(2-hydroxyethyl)terephthalate which comprises:
    (1) a crystallization step of cooling an ethylene glycol solution containing crude bis(2-hydroxyethyl)terephthalate from a temperature of at least saturation solubility to temperatures ranging from 15 to 30° C. and keeping the solution within the temperature range for 2 to 12 hours, and wherein the solution is obtained by decomposing post-consumer PET bottles by use of ethylene glycol, and the solution contains a solute in an amount of 5 to 40 wt % and 2-hydroxyethyl[2-(2-hydroxyethoxy)ethyl] terephthalate in an amount of 1 to 8 wt % based on all solutes, and
    (2) a solid-liquid separation step of subjecting a precipitate containing bis(2-hydroxyethyl)terephthalate as a main component to solid-liquid separation while keeping the precipitate within a temperature range of 15 to 30° C. so as to obtain a cake comprising bis(2-hydroxyethyl)terephthalate as a main component.

2. The method of claim 1, wherein the total content of solutes in the ethylene glycol solution containing crude bis(2-hydroxyethyl)terephthalate is 10 to 30 wt %.

3. The method of claim 1, wherein the ethylene glycol solution containing crude bis(2-hydroxyethyl)terephthalate is a solution containing a gas barrier agent component as an accessory solute.

4. The method of claim 1, wherein the ethylene glycol solution containing crude bis(2-hydroxyethyl)terephthalate is a solution having an electric conductivity of 0.2 to 0.6 µS/cm.

5. The method of claim 1, wherein the ethylene glycol solution containing crude bis(2-hydroxyethyl)terephthalate is a solution obtained by decomposing post-consumer PET bottles by use of ethylene glycol and then decolorizing and deionizing a decomposition product.

6. The method of claim 5, wherein the post-consumer PET bottles are colored PET bottles containing an ultraviolet blocking agent.

7. The method of claim 1, wherein the precipitate has an average particle diameter of 40 to 200 µm.

8. The method of claim 1, wherein the precipitate containing bis(2-hydroxyethyl)terephthalate as a main component is subjected to solid-liquid separation by use of a filter press using a filter fabric having an air permeability of 3 to 30 cm$^3$/min·cm$^2$.

9. A method of purifying bis(2-hydroxyethyl )terephthalate which comprises:
    (1) evaporation steps comprising:
    (a) a first evaporation step of introducing an ethylene glycol solution containing crude bis(2-hydroxyethyl) terephthalate obtained by decomposing post-consumer PET bottles by use of ethylene glycol into a first evaporator and evaporating low-boiling-point components at a temperature of 130 to 170° C. and a pressure of 300 to 1,000 Pa so as to obtain a first melt solution having a total content of ethylene glycol and free diethylene glycol of 3 to 10 wt %, and
    (b) a second evaporation step of introducing the first melt solution into a second evaporator and evaporating low-boiling-point components at a temperature of 130 to 170° C. and a pressure of 50 to 250 Pa so as to obtain a second melt solution having a total content of ethylene glycol and free diethylene glycol of not higher than 0.45 wt %, and
    (2) a molecular distillation step of introducing the second melt solution into a falling-thin-film type molecular still and distilling the solution at a temperature of 180 to 220° C. and a pressure of not higher than 25 Pa so as to obtain a fraction containing bis(2-hydroxyethyl) terephthalate as a main component and having a 2-hydroxyethyl[2-(2-hydroxyethoxy)ethyl]terephthalate content of not higher than 1.5 wt % and an oligomer content of not higher than 1 wt %.

10. The method of claim 9, wherein the total content of solutes in the ethylene glycol solution containing crude bis(2-hydroxyethyl)terephthalate is 5 to 85 wt %.

11. The method of claim 9, wherein the ethylene glycol solution containing crude bis(2-hydroxyethyl)terephthalate is a solution containing, as an accessory solute, 2-hydroxyethyl[2-(2-hydroxyethoxy)ethyl]terephthalate in an amount of 1 to 8 wt % based on all solutes.

12. The method of claim 9, wherein the ethylene glycol solution containing crude bis(2-hydroxyethyl)terephthalate is a solution having an electric conductivity of 0.2 to 0.6 µS/cm.

13. The method of claim 9, wherein the ethylene glycol solution containing crude bis(2-hydroxyethyl)terephthalate is a solution obtained by decomposing post-consumer PET bottles by use of ethylene glycol and then decolorizing and deionizing a decomposition product or a solution resulting from melting a cake obtained by subjecting the solution to crystallization and separation by filtration.

14. The method of claim 9, wherein the total of the content of free diethylene glycol in a condensate obtained by cooling the low-boiling-point components from the evaporation steps and the content of free diethylene glycol in the second melt solution is 2 wt % or lower of the total of the amounts of the condensate and the second melt solution.

15. The method of claim 9, wherein the content of the oligomer in the second melt solution is 15 wt % or lower.

16. The method of claim 9, wherein the weight ratio of the fraction to a distillation pot residue in the molecular distillation step is 9:1 to 5:5.

17. The method of claim 9, wherein the low-boiling-point components evaporated in the first evaporation step are used as at least a portion of a cooling medium for a condenser in the molecular distillation step.

18. A method of purifying bis(2-hydroxyethyl)terephthalate which comprises:
(1) a crystallization step of cooling an ethylene glycol solution containing crude bis(2-hydroxyethyl)terephthalate from a temperature of at least saturation solubility to temperatures ranging from 15 to 30° C. and keeping the solution within the temperature range for 2 to 12 hours and wherein the solution is obtained by decomposing post-consumer PET bottles by use of ethylene glycol, and the solution contains a solute in an amount of 5 to 40 wt % and 2-hydroxyethyl[2-(2-hydroxyethoxy)ethyl] terephthalate in an amount of 1 to 8 wt % based on all solutes,
(2) a solid-liquid separation step of subjecting a precipitate containing bis(2-hydroxyethyl)terephthalate as a main component to solid-liquid separation while keeping the precipitate within a temperature range of 15 to 30° C. so as to obtain a cake comprising bis(2-hydroxyethyl)terephthalate as a main component,
(3) evaporation steps comprising:
(a) a first evaporation step of introducing a melt solution of the cake into a first evaporator and evaporating low-boiling-point components at a temperature of 130 to 170° C. and a pressure of 300 to 1,000 Pa so as to obtain a first melt solution having a total content of ethylene glycol and free diethylene glycol of 3 to 10 wt %, and
(b) a second evaporation step of introducing the first melt solution into a second evaporator and evaporating low-boiling-point components at a temperature of 130 to 170° C. and a pressure of 50 to 250 Pa so as to obtain a second melt solution having a total content of ethylene glycol and free diethylene glycol of not higher than 0.45 wt %, and
(4) a molecular distillation step of introducing the second melt solution into a falling-thin-film type molecular still and distilling the solution at a temperature of 180 to 220° C. and a pressure of not higher than 25 Pa so as to obtain a fraction containing bis(2-hydroxyethyl)terephthalate as a main component and having a 2-hydroxyethyl[2-(2-hydroxyethoxy)ethyl]terephthalate content of not higher than 1.5 wt % and an oligomer content of not higher than 1 wt %.

19. The method of claim 18, wherein the total content of solutes in the ethylene glycol solution containing crude bis(2-hydroxyethyl)terephthalate is 10 to 30 wt %.

20. The method of claim 18, wherein the ethylene glycol solution containing crude bis(2-hydroxyethyl)terephthalate is a solution containing a gas barrier agent component as an accessory solute.

21. The method of claim 18, wherein the ethylene glycol solution containing crude bis(2-hydroxyethyl)terephthalate is a solution having an electric conductivity of 0.2 to 0.6 µS/cm.

22. The method of claim 18, wherein the ethylene glycol solution containing crude bis(2-hydroxyethyl)terephthalate is a solution obtained by decomposing post-consumer PET bottles by use of ethylene glycol and then decolorizing and deionizing a decomposition product.

23. The method of claim 22, wherein the post-consumer PET bottles are colored PET bottles containing an ultraviolet blocking agent.

24. The method of claim 18, wherein the cooled ethylene glycol solution containing crude bis(2-hydroxyethyl)terephthalate is kept within the temperature range of 15 to 30° C. for 1 to 12 hours.

25. The method of claim 18, wherein the precipitate has an average particle diameter of 40 to 200 µm.

26. The method of claim 18, wherein the precipitate containing bis(2-hydroxyethyl)terephthalate as a main component is subjected to solid-liquid separation by use of a filter press using a filter fabric having an air permeability of 3 to 30 cm³/min·cm².

27. The method of claim 18, wherein the total of the content of free diethylene glycol in a condensate obtained by cooling the low-boiling-point components from the evaporation steps and the content of free diethylene glycol in the second melt solution is 2 wt % or lower of the total of the amounts of the condensate and the second melt solution.

28. The method of claim 18, wherein the content of the oligomer in the second melt solution is 15 wt % or lower.

29. The method of claim 18, wherein the weight ratio of the fraction to a distillation pot residue in the molecular distillation step is 9:1 to 5:5.

* * * * *